United States Patent
Teranishi et al.

(10) Patent No.: US 9,528,971 B2
(45) Date of Patent: Dec. 27, 2016

(54) PARTICULATE MATTER DETECTION ELEMENT AND METHOD OF MANUFACTURING SAME

(71) Applicant: DENSO CORPORATION, Kariya, Aichi-pref. (JP)

(72) Inventors: Shinya Teranishi, Aichi-ken (JP); Tekehito Kimata, Kariya (JP); Noriaki Kihara, Okazaki (JP)

(73) Assignee: DENSO CORPORATION, Kariya (JP)

( * ) Notice: Subject to any disclaimer, the term of this patent is extended or adjusted under 35 U.S.C. 154(b) by 420 days.

(21) Appl. No.: 13/845,998

(22) Filed: Mar. 18, 2013

(65) Prior Publication Data

US 2013/0283886 A1    Oct. 31, 2013

(30) Foreign Application Priority Data

Apr. 27, 2012  (JP) ................. 2012-102709

(51) Int. Cl.
| | | |
|---|---|---|
| G01N 7/00 | (2006.01) | |
| G01N 33/00 | (2006.01) | |
| G01N 15/06 | (2006.01) | |
| G01N 15/00 | (2006.01) | |

(52) U.S. Cl.
CPC ...... *G01N 33/0047* (2013.01); *G01N 15/0606* (2013.01); *G01N 15/0656* (2013.01); *G01N 2015/0046* (2013.01)

(58) Field of Classification Search
CPC ................................. G01N 33/0047
USPC ....................................... 73/23.31
See application file for complete search history.

(56) References Cited

U.S. PATENT DOCUMENTS

| | | | |
|---|---|---|---|
| 6,634,210 B1* | 10/2003 | Bosch | G01N 15/0656 204/426 |
| 8,419,915 B2* | 4/2013 | Furuta et al. | 204/424 |
| 2007/0173711 A1* | 7/2007 | Shah et al. | 600/347 |
| 2008/0265870 A1* | 10/2008 | Nair | G01N 15/0656 324/105 |
| 2009/0051376 A1 | 2/2009 | Schnell et al. | |
| 2010/0147052 A1* | 6/2010 | Nelson et al. | 73/28.01 |
| 2012/0047991 A1 | 3/2012 | Tokuda et al. | |

FOREIGN PATENT DOCUMENTS

| | | |
|---|---|---|
| JP | 60-196659 | 10/1985 |
| JP | 63-066859 | 3/1988 |
| JP | 64-047067 | 2/1989 |

(Continued)

OTHER PUBLICATIONS

Office Action (2 pages) dated Feb. 25, 2014, issued in corresponding Japanese Application No. 2012-102709 and English translation (3 pages).

*Primary Examiner* — Hezron E Williams
*Assistant Examiner* — Tarun Sinha
(74) *Attorney, Agent, or Firm* — Nixon & Vanderhye P.C.

(57) ABSTRACT

The particulate matter detection element is constituted of a laminated body including first and second electrode layers each having a plate-like shape and a thickness between 50 μm and 500 μm laminated on each other through an intermediate insulating layer having a plate-like shape and a thickness between 3 μm and 20 μm. A cross-sectional surface of the laminated body in the lamination direction is used as a detection surface of the particulate matter detection element.

10 Claims, 26 Drawing Sheets

(56) References Cited

FOREIGN PATENT DOCUMENTS

| JP | 03-087079 | 4/1991 |
| JP | 03-174783 | 7/1991 |
| JP | 09-153649 | 6/1997 |
| JP | 2005-164554 | 6/2005 |
| JP | 2005-316037 | 11/2005 |
| JP | 2008-502892 | 1/2008 |
| JP | 2012-047596 | 3/2012 |
| JP | 2012-078130 | 4/2012 |
| JP | 2012-083121 | 4/2012 |

* cited by examiner

COMPARATIVE EXAMPLE

COMPARATIVE EXAMPLE

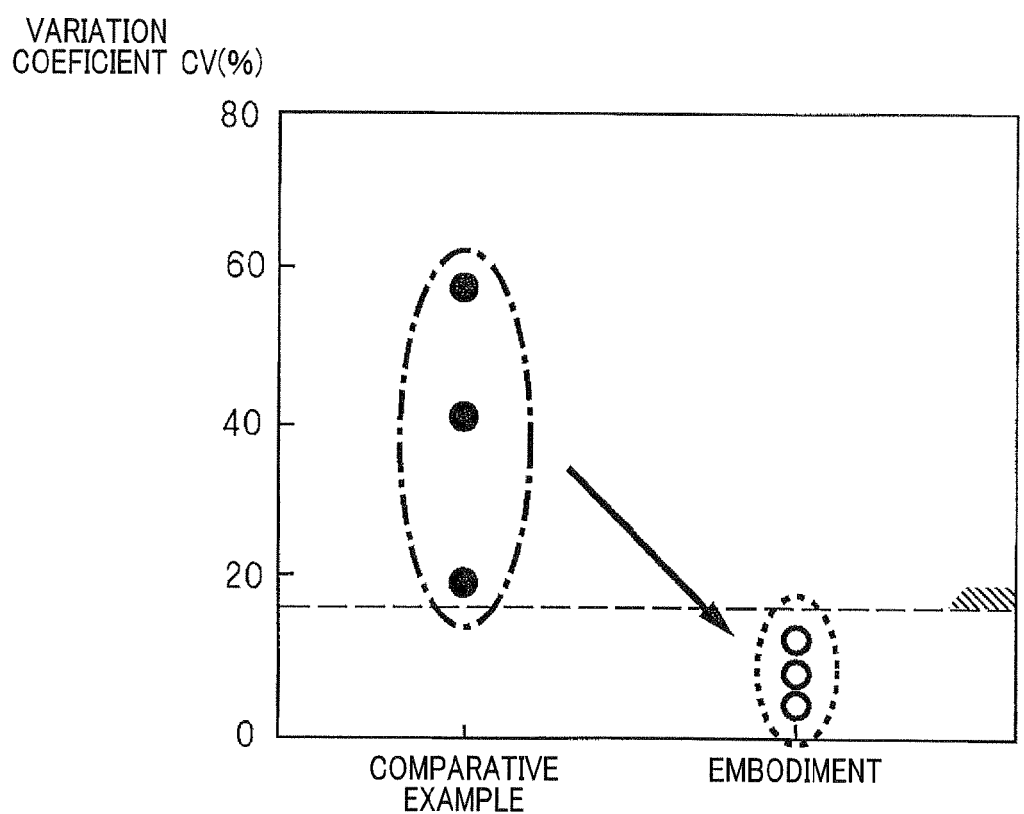

PARTICULATE MATTER DETECTION ELEMENT AND METHOD OF MANUFACTURING SAME

This application claims priority to Japanese Patent Application No. 2012-102709 filed on Apr. 27, 2012, the entire contents of which are hereby incorporated by reference.

BACKGROUND OF THE INVENTION

1. Field of the Invention

The present invention relates to a particulate matter detection element for detecting particulate matter consisting primarily of soot made up of carbon contained in a measured gas emitted from an internal combustion engine of a vehicle, for example, and relates to a method of manufacturing the particulate matter detection element.

2. Description of Related Art

It is known to provide a diesel particulate filter (referred to as "DPF" hereinafter) in an exhaust gas passage of a vehicle-use diesel engine or the like to collect environmental pollutant contained in exhaust gas, particularly, soot particles and particulate matter (may be referred to as "PM" hereinafter) composed mostly of SOF (soluble organic fraction). The DPF, which is made of a porous ceramic having high resistance to heat, collects PM while the exhaust gas passes through partition walls having many pores. If a collection amount of PM exceeds a permissible value, the pressure drop of the DPF increases due to clogging, and the DPF may be broken by a heat generated at the time of burning off collected PM, causing PM to directly pass through the DPF.

There are many proposals for PM detection sensors for detecting PM contained in a measured gas, which enables determining an appropriate time to regenerate a DPF, and early and reliable detection of an abnormality such as passing of PM directly through the DPF. For example, Japanese Patent Application Laid-open No. 2005-164554 discloses a PM detection element in which PM contained in a measured gas is collected between a pair of comb-shaped electrodes disposed on the surface of an insulator so as to be opposed to each other, and the PM content of the measured gas is determined by measuring an electrical characteristic such as resistance, capacitance or impedance between the pair of the comb-shaped electrodes, which vary depending on the collection amount of PM. For another example, Japanese Patent Application Laid-open No. 2012-47596 discloses a particulate matter detection device including an element-base material of a plate-like shape, a pair of measuring electrodes disposed in the element-base material, a characteristic measuring means for measuring an electrical characteristic between the pair of the measuring electrodes, and calculating means for calculating an amount of particulate matter collected in and in the vicinity of the pair of the measuring electrodes, based on the electrical characteristic measured by the characteristic measuring means, where each of the measuring electrodes is a comb-shaped electrode including a plurality of substantially planar comb tooth portions and a comb base portion connecting the comb tooth portions together at their ends, the comb tooth portions of one of the measuring electrodes and the comb tooth portions of the other measuring electrode being located so as to alternate with each other, the comb base portion of at least one of the measuring electrodes being covered by a comb base covering portion made of dielectric. This particulate matter detection device detects PM trapped in or in the vicinity of the pair of the measuring electrodes by measuring variation of an electrical characteristic between the pair of the measuring electrodes.

Such a conventional PM detection element is formed to have a comb pattern in which a plurality of reed-shaped electrodes are disposed spaced out from one another so that different polarities alternate on the surface of an insulating substrate such as alumina or a conductive substrate such as zirconia, using a thick film printing method or a thin film printing method such as chemical vapor deposition (CVD) or physical vapor deposition (PVD). There is a dead mass in such a PM detection element including the comb-shaped electrodes opposed to each other. Before the mass of PM collected between the comb-shaped electrodes exceeds the dead mass, the PM detection element cannot sense PM. Accordingly, it is necessary to reduce the dead mass as much as possible to enable early and reliable detection of an abnormality of the PDF.

On the other hand, if the mass of PM collected between the comb-shaped electrodes exceeds a certain limit value, since the electrical characteristic between the comb-shaped electrodes becomes saturated and remains unchanged, PM contained in the measured gas cannot be measured. Accordingly, the PM detection device as described above is configured to burn off PM collected between the comb-shaped electrodes when the amount of collected PM reaches the limit value using a heater to regenerate the PDF.

However, when the comb-shaped electrodes are formed using a common thick film printing method, the distance between the adjacent comb tooth portions is about 20 μm at minimum because of rheology characteristics of a printing paste used and constraints in manufacturing masks to be formed in a printing screen. On the other hand, when the comb-shaped electrodes are formed using a thin film printing method such as CVD or PVD, although it is possible to form an extremely fine pattern, the facility cost therefor becomes very high. Accordingly, the manufacturing cost increases in this case. In addition, since the comb-shaped electrodes are inevitably a thin film, when they are used in a severe atmosphere in which they are subjected to a thermal stress occurring at the time of burning off collected PM, or a hot/cold stress due to moisture contained in the measured gas, the comb-shaped electrodes may evaporate or flake off.

Further, it was found that if the pair of the comb-shaped electrodes are formed such that the distance between the adjacent comb tooth portions is in the order of 20 to 50 μm using a common thick film printing method, the dead mass is inadmissibly large and varies greatly from device to device as explained later.

SUMMARY

An exemplary embodiment provides a particulate matter detection element for detecting particulate matter contained in a measured gas comprising:

at least one pair of detection electrodes disposed opposite to each other on a detection surface of the particulate matter detection element; and an output means for outputting a signal representing one of a resistance, a capacitance and a impedance between the pair of the detection elements as an electrical characteristic varying depending on an amount of particulate matter present between the pair of the detection electrodes;

wherein the pair of the detection electrodes is constituted as an electrode layer laminated body in which first and second electrode layers each having a plate-like shape and a thickness in a range between 50 μm and 500 μm are laminated on each other through an intermediate insulating layer having a plate-like shape and a thickness in a range between 3 μm and 20 μm, and a cross-sectional surface in a lamination direction of the electrode layer laminated body exposed to outside is used as the detection surface of the particulate matter detection element.

The exemplary embodiment also provides a method of manufacturing the particulate matter detection element, comprising:

an electrode layer forming step of forming a first green sheet for a first electrode layer and a second green sheet for a second electrode layer each having a plate-like shape and a thickness in a range between 50 μm and 500 μm using a perovskite-type conductive oxide metal selected from LNF ($LaNi_{0.6}Fe_{0.4}O_3$), LSN ($La_{1.2}Sr_{0.8}NiO_4$) LSM ($La_{1-x}Sr_xMnO_{3-\delta}$), LSC ($La_{1-x}Sr_xCoO_{3-\delta}$), LCC ($La_{1-x}Ca_xCrO_{3-\delta}$), and LSCN ($La_{0.85}Sr_{0.15}Cr_{1-x}NiXO_{3-\delta}$) ($0.1 \leq X \leq 0.7$);

an insulating layer forming step of forming a third green sheet for an intermediate insulating layer having a plate-like shape and a thickness in a range between 3 μm and 20 μm using an insulating oxide material selected from a partially stabilized zirconia typified by $8YSZ((ZrO_2)_{0.82}(Y_2O_3)_{0.08})$, MgO and $Al_2O_3$; and a laminated body forming step of forming the electrode layer laminated body by laminating the first to third green sheets.

The exemplary embodiment also provides a method of manufacturing the particulate matter detection element, comprising:

an electrode layer forming step of forming a first green sheet for a first electrode layer and a second green sheet for a second electrode layer each having a plate-like shape and a thickness in a range between 50 μm and 500 μm using a perovskite-type conductive oxide material selected from LNF ($LaNi_{0.6}Fe_{0.4}O_3$), LSN ($La_{1.2}Sr_{0.8}NiO_4$), LSM ($La_{1-x}Sr_xMnO_{3-\delta}$), LSC ($La_{1-x}Sr_xCoO_{3-\delta}$), LCC ($La_{1-x}Ca_xCrO_{3-\delta}$), and LSCN ($La_{0.85}Sr_{0.15}Cr_{1-x}NiXO_{3-\delta}$) ($0.1 \leq X \leq 0.7$);

an insulating layer forming step of print-forming an intermediate insulating layer film having a plate-like shape and a thickness in a range between 3 μm and 20 μm on a surface of each of the first and second green sheets using an insulating oxide material selected from a partially stabilized zirconia typified by $8YSZ((ZrO_2)_{0.82}(Y_2O_3)_{0.08})$, MgO and $Al_2O_3$; and a laminated body forming step of forming the electrode layer laminated body by laminating the first and second green sheets formed with the intermediate insulating layer film.

The exemplary embodiment also provides particulate matter detection sensor comprising:

the particulate material detection element as recited above; and an electrical characteristic detection means for determining an amount of particulate matter collected between the pair of the detection electrodes based on the signal outputted from the output means According to the exemplary embodiment, there is provided a particulate matter detection element and a particulate matter detection sensor having a sufficiently small dead mass, and a sufficiently small element-to-element or sensor-to-sensor variation in detection accuracy.

Other advantages and features of the invention will become apparent from the following description including the drawings and claims.

BRIEF DESCRIPTION OF THE DRAWINGS

In the accompanying drawings:

FIG. 8B is a diagram for explaining advantages of the invention regarding variation in detection while referring to the comparative example;

PREFERRED EMBODIMENTS OF THE INVENTION

First Embodiment

Figure 1A:
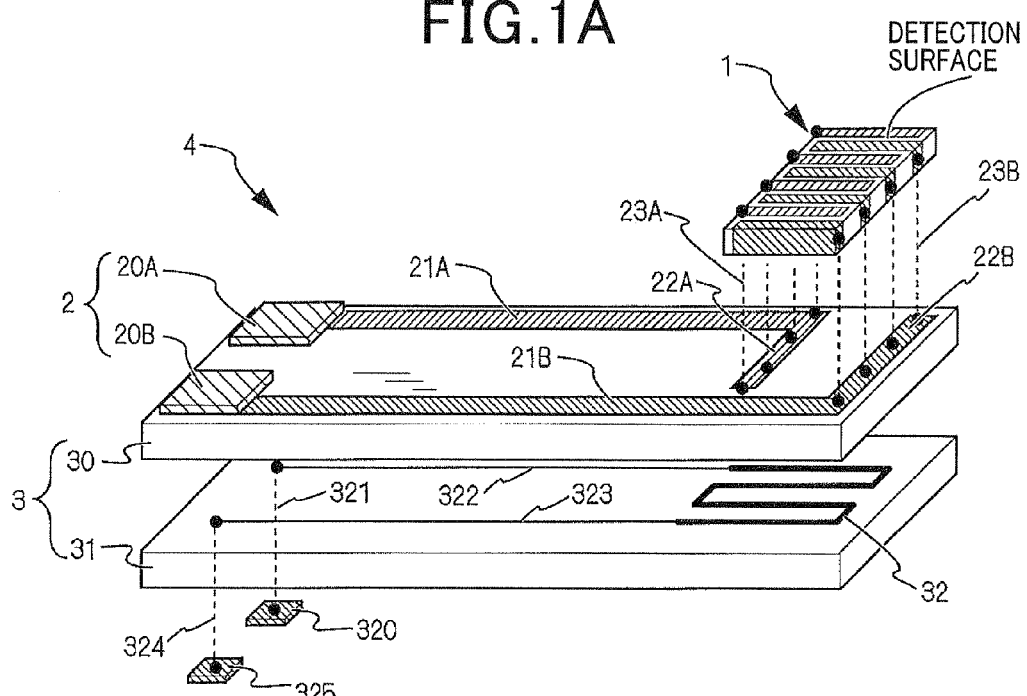
FIG. 1A is a perspective view showing a PM detection element according to a first embodiment of the invention.

A PM (particulate matter) detection element 4 (may be referred to as the detection element 4 hereinafter) according to a first embodiment of the invention is described with reference to FIGS. 1A, 1B and 1C. As shown in FIG. 1A, the detection element 4 has a structure in which an electrode drawing layer 2 is formed on the surface of an insulating substrate 3 having a plate-like shape, and an electrode layer laminated body 1 (may be referred to as the laminated body 1 hereinafter) is mounted on the front end portion of the insulating substrate 3 which is exposed to a measured gas.

Figure 1B:
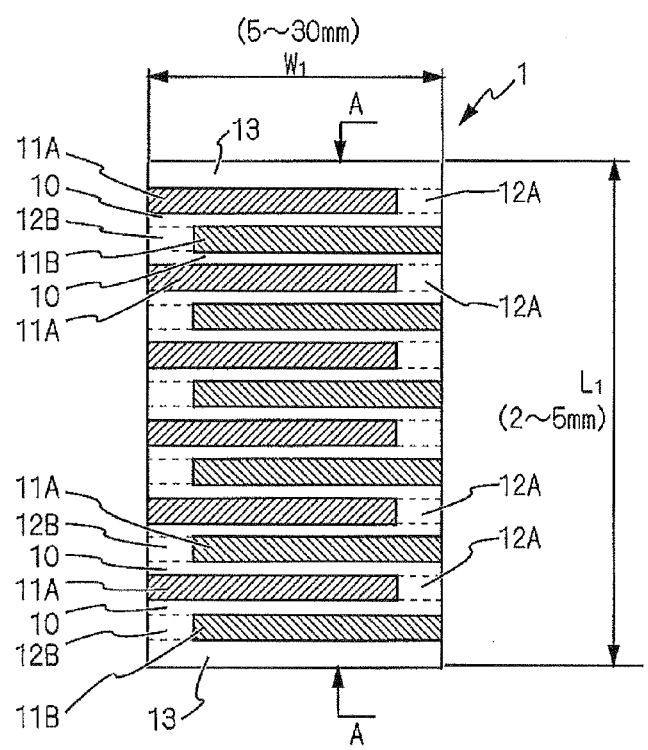
FIG. 1B is a plan view showing an electrode layer laminated body of the PM detection element shown in FIG. 1A.
Figure 1C:
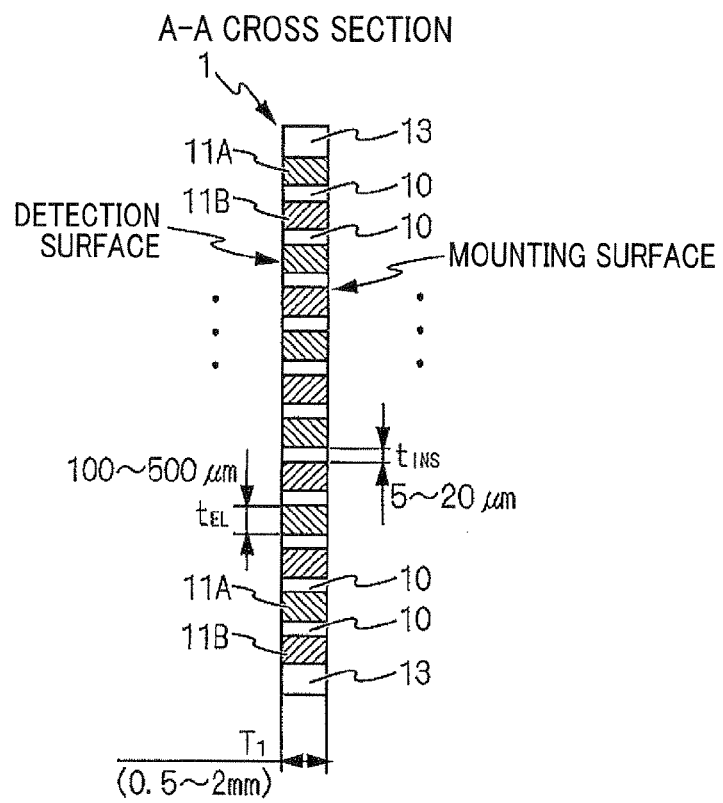
FIG. 1C is a cross-sectional view of FIG. 1B taken along line A-A.

As shown in FIGS. 1B and 1C, the laminated body 1 has a laminated structure in which a plurality of first and second electrode layers 11A and 11B made of a conductive oxide and having a plate-like shape and intermediate insulating layers 10 made of an insulating oxide are laminated alternately on one another and are baked together. One end of the first electrode layer 11A is exposed from one lateral side of the laminated body 11, and the other end of the first electrode layer 11A is covered by a first end-portion insulating layer 12A. One end of the second electrode layer 11B on the side on which the first electrode layer 11A is drawn is covered by a second end-portion insulating layer 12B, and the other end of the second electrode layer 11B is exposed from the other lateral side of the laminated body 11. The ends of the first electrode layers 11A and the ends of the second electrode layers 11B, which are exposed respectively from the opposite lateral sides of the laminated body 11 in an alternate manner, are electrically connected to a first land portion 22A and a second land portion 22B, respectively, which are formed on the surface of the insulating substrate 3 through a first junction means 23A and a second junction means 23B, respectively. The plurality of the first electrode layers 11A and the plurality of the second electrode layers 11B constitute a pair of comb-shaped electrodes opposite to each other with the intermediate insulating layers 10 disposed therebetween. The laminated body 1 includes a terminal insulating layer 13 at each of the upper and lower terminal portions thereof.

The electrode drawing layer 2 includes the first land portion 22A, a first lead portion 21A connected to the first land portion 22A and a first terminal portion 20A connected to the first lead portion 21A. The electrode drawing layer 2 also includes the second land portion 22B, a second lead portion 21B connected to the second land portion 22B and a second terminal portion 20B connected to the second lead portion 21B. The electrode drawing layer 2 enables electrical connection between the laminated body 1 and the outside, and fixation of the laminated body 1 to the insulating substrate 3. The first and second terminal portions 20A and 20B, the first and second lead portions 21A and 21B, and the first and second land portions 22A and 22B can be formed by a known electrode forming method such as a thick film printing method, a vapor deposition method or a plating method using an appropriate conductive material such as Al, Ti, Cr, Ni, Cu, Pd, Ag, W, Pt or Au.

The first and second junction means 23A and 23B may be soldering or brazing. In a case where the first and second electrode layers 11A and 11B are soldered respectively to the first and second land portions 22A and 22B, the surfaces of the first and second electrode layers 11A and 11B may be formed with a metal film having a good solder wettability such as nickel or Cu. If the material of the first and second land portions 22A and 22B is the same as the material of the first and second electrode layers 11A and 11B, it is possible to establish the electrical connection and the fixation between the laminated body 1 and the insulating substrate 3 by baking them together.

The layer thickness $t_{EL}$ of the first and second electrode layers 11A and 11B is from 50 μm to 500 μm. The layer thickness $t_{INS}$ of the intermediate insulating layer 10 is from 3 μm to 20 μm. The laminated body 1 as a detection part including the first electrode layers 11A, the second electrode layers 11B and the intermediate insulating layers 10 laminated alternately is formed in a plate-like shape having a thickness $T_1$ (from 0.5 mm to 2.0 mm in this embodiment), a width $W_1$ (from 5.0 mm to 30.0 mm in this embodiment) and a length $L_1$ (from 2.0 mm to 5.0 mm in this embodiment). The end surfaces of the respective layers in the film thickness direction are used as a detection surface such that the layer thickness $t_{EL}$ of the first and second electrode layers 11A and 11B is the width of the pair of the comb-shaped electrodes each having a pair of detection electrodes, and the layer thickness $t_{INS}$ of the intermediate insulating layers 10 is a distance between the adjacent detection electrodes. Hence, according to this embodiment, the intermediate insulating layers 10 having the thin thickness and the first and second electrode layers 11A and 11B having the thick thickness can be formed with a very high degree of accuracy compared to the conventional case where the comb-shaped electrodes are formed using a common thick film printing method.

The first and second electrode layers 11A and 11B may be made of a perovskite-type conductive oxide selected from LNF (LaNi$_{0.6}$Fe$_{0.4}$O$_3$), LSN (La$_{1.2}$Sr$_{0.8}$NiO$_4$), LSM (La$_{1-x}$Sr$_x$MnO$_{3-\delta}$), LSC (La$_{1-x}$Sr$_x$CoO$_{3-\delta}$), LCC (La$_{1-x}$Ca$_x$CrO$_{3-\delta}$), and LSCN (La$_{0.85}$Sr$_{0.15}$Cr$_{1-x}$NiXO$_{3-\delta}$) (0.1≤X≤0.7). The intermediate insulating layer 10 and the first and second end-portion insulating layers 12A and 12B may be made of an insulating oxide selected from a partially stabilized zirconia typified by 8YSZ(ZrO$_2$)$_{0.82}$(Y$_2$O$_3$)$_{0.08}$), MgO and Al$_2$O$_3$.

The electrical conductivities of the first and second electrode layers 11A and 11B are lower than or equal to $10^{-2}$ S/cm. The electrical conductivities of the intermediate insulating layer 10 and the first and second end-portion insulating layers 12A and 12B are lower than or equal to $10^{-5}$ S/cm.

The insulating substrate 3 includes therein a heater 32 made of a metal or an alloy of Al, Ti, Cr, Ni, Cu, Pd, Ag, W, Pt or Au, and disposed between insulating layers 30 and 31 made of an insulating material such as alumina formed in a plate-like shape by a doctor blade method or the like. The detection element 4 can be regenerated by passing a current to the heater 32 to burn off PM collected in the laminated body 1. The heater 32 is connected with a heater lead portions 322 and 323, through hole conductors 321 and 324, and heater terminal portions 320 and 325. A current supply control device (not shown) is connected to the heater terminal portions 320 and 325 so that the heater 32 can be supplied with a current to heat the laminated body 1 as necessary.

Next, a method of manufacturing the laminated body 1 and the PM detection element 4 is explained with reference to Figs. FIG. 2A, FIG. 2B, FIG. 2C, FIG. 2D, FIG. 2E, FIG. 2F, FIG. 3A, FIG. 3B, FIG. 4, FIG. 5A, FIG. 5B, FIG. 6A and FIG. 6B.

First, an electrode layer slurry is prepared by mixing a material which forms the conductive oxide after being baked with binder, disperser and dispersion medium. Subsequently, an electrode layer forming step is performed by a doctor blade method or the like on the prepared slurry to form a green sheet 110 for the electrode layers (referred to as the electrode layer sheet 110 hereinafter). The electrode layer sheet 110 is formed so as to have the layer thickness $t_{EL}$ in a range from 50 μm to 500 μm after being baked.

Next, an insulating layer slurry is prepared by mixing a material which forms the insulating oxide after being baked with binder, disperser and dispersion medium. Subsequently, an insulating layer forming step is performed by a doctor blade method or the like on the prepared slurry to form a green sheet 120 for the end-portion insulating layers (referred to as the end-portion insulating layer sheet 120 hereinafter) having the same thickness as the electrode layer sheet 110. Further, a green sheet 100 for the intermediate insulating layers (referred to as the intermediate insulating layer sheet 100 hereinafter) is formed by a doctor blade method or the like using the same insulating layer slurry as that of the end-portion insulating layer sheet 120.

The intermediate insulating layer sheet 100 is formed so as to have the layer thickness $t_{INS}$ in a range from 3 μm to 20 μm after being baked. Incidentally, since the thickness of the intermediate insulating layer sheet 100 after being baked is as thin as 20 μm or below, it may be formed by a thick film printing method using an insulating layer paste prepared by mixing the material which forms the insulating oxide after being baked with binder, disperser and dispersion medium.

Figure 2A:
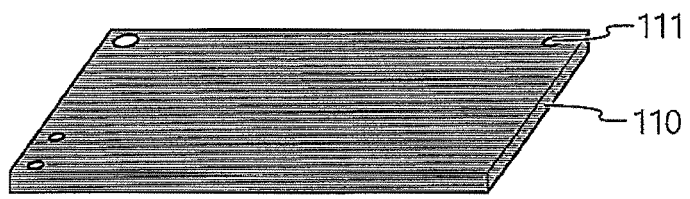
FIG. 2A is a perspective view for explaining a step of preparing a green sheet for an electrode layer used for a method of manufacturing the PM detection element according to the first embodiment.
Figure 2B:
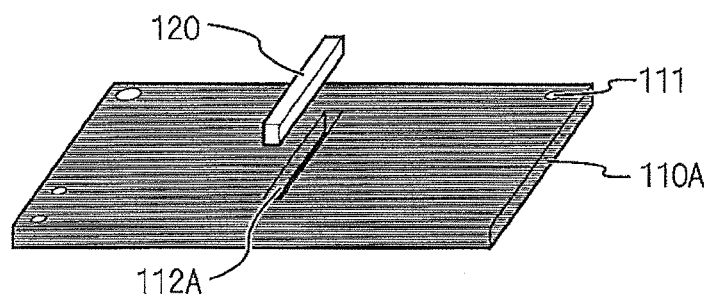
FIG. 2B is a perspective view for explaining a step of embedding a first end-portion insulating layer performed after the step shown in FIG. 2A.

Next, a step of forming the end-insulating layer is explained. As shown in FIG. 2A, the electrode layer sheet is punched out to a predetermined shape as an electrode layer sheet 110A using a die, and perforated with a positioning hole 111 at a predetermined position for passing through a positioning guide pin. Next, as shown in FIG. 2B, the electrode layer sheet 110A is perforated with an insulating layer embedding hole 112A (referred to as the embedding hole 112A hereinafter) at a predetermined position (the center position in this embodiment) for forming first end-portion insulating layers 12A. Subsequently, the end-portion insulating layer sheet 120 is punched out so as to have the same thickness as the electrode layer sheet 110 and the same size as the embedding hole 112A is embedded into the embedding hole 112A. As a result, a first electrode layer sheet 110A/120 is obtained. The electrode layer sheet 110 and the end-portion insulating layer sheet 120 may be punched in an overlapped state at the same time using the die for forming the embedding hole 112A so that the end-portion insulating layer sheet 120 can be tightly embedded into the electrode layer sheet 12. Alternately, the first electrode layer sheet 110A/120 may be formed by filling an embedding hole 112A formed in advance in the electrode layer sheet 110 with the insulating layer slurry, and thereafter drying the slurry.

Figure 2C:
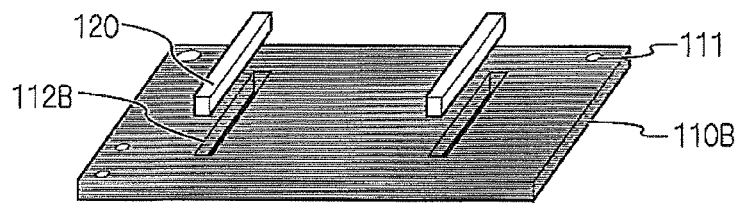
FIG. 2C is a perspective view for explaining a step of embedding a second end-portion insulating layer performed after the step shown in FIG. 2B.

Next, as shown in FIG. 2C, the electrode layer sheet is punched out to a predetermined shape as an electrode layer sheet 110B using a die. The electrode layer sheet 110B is perforated with two insulating layer embedding holes 112B (referred to as the embedding holes 112B hereinafter) at predetermined positions for forming the second end-portion insulating layers 12B. Subsequently, the end-portion insulating layer sheet 120 is embedded into the embedding holes 112B. As a result, a second electrode layer sheet 110B/120 is obtained.

Figure 2D:
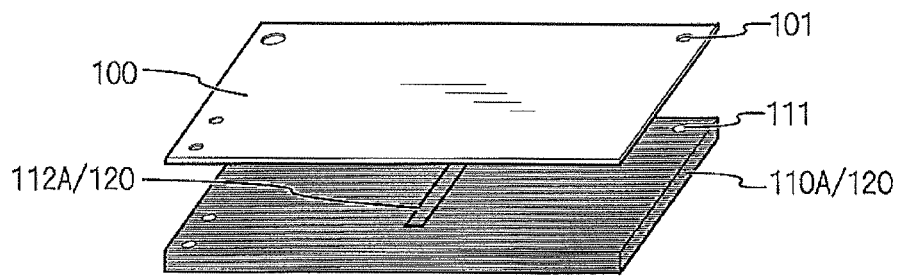
FIG. 2D is a perspective view for explaining a step of forming an intermediate insulating layer performed after the step shown in FIG. 2B.
Figure 2E:
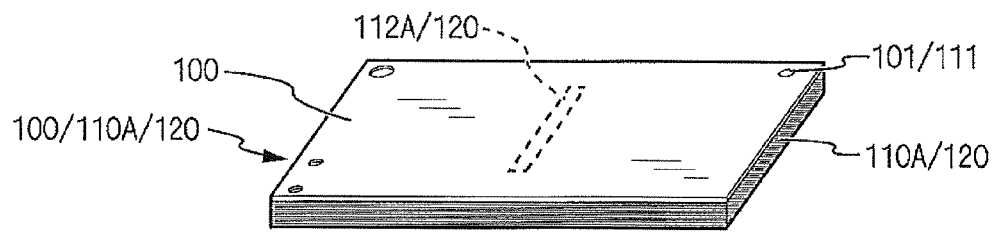
FIG. 2E is a perspective view of a first electrode layer green sheet formed with the first end-portion insulating layer and the intermediate insulating layer obtained after the step shown in FIG. 2D.
Figure 2F:
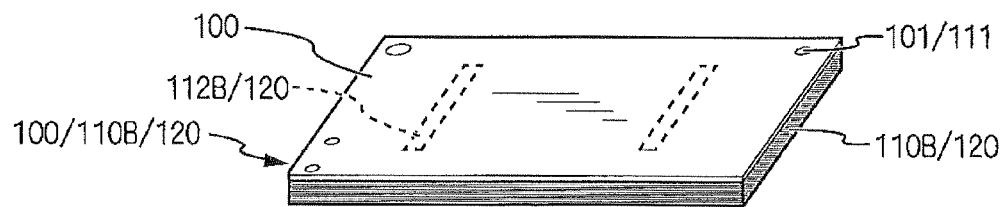
FIG. 2F is a perspective view of a second electrode layer green sheet formed with the second end-portion insulating layer and the intermediate insulating layer obtained after the step shown in FIG. 2C.

As shown in FIG. 2D, in the laminated body forming step, the obtained first electrode layer sheet 110A/120 and the intermediate insulating layer sheet 100 perforated with a positioning hole 101 in advance are laminated on each other aligning their positioning holes 111 and 101 to form a first laminated sheet 100/110A/120 shown in FIG. 2E. Likewise, the second electrode layer sheet 110B/120 and the intermediate insulating layer sheet 100 are laminated on each other to form a second laminated sheet 100/110B/120 shown in FIG. 2F.

Figure 3A:
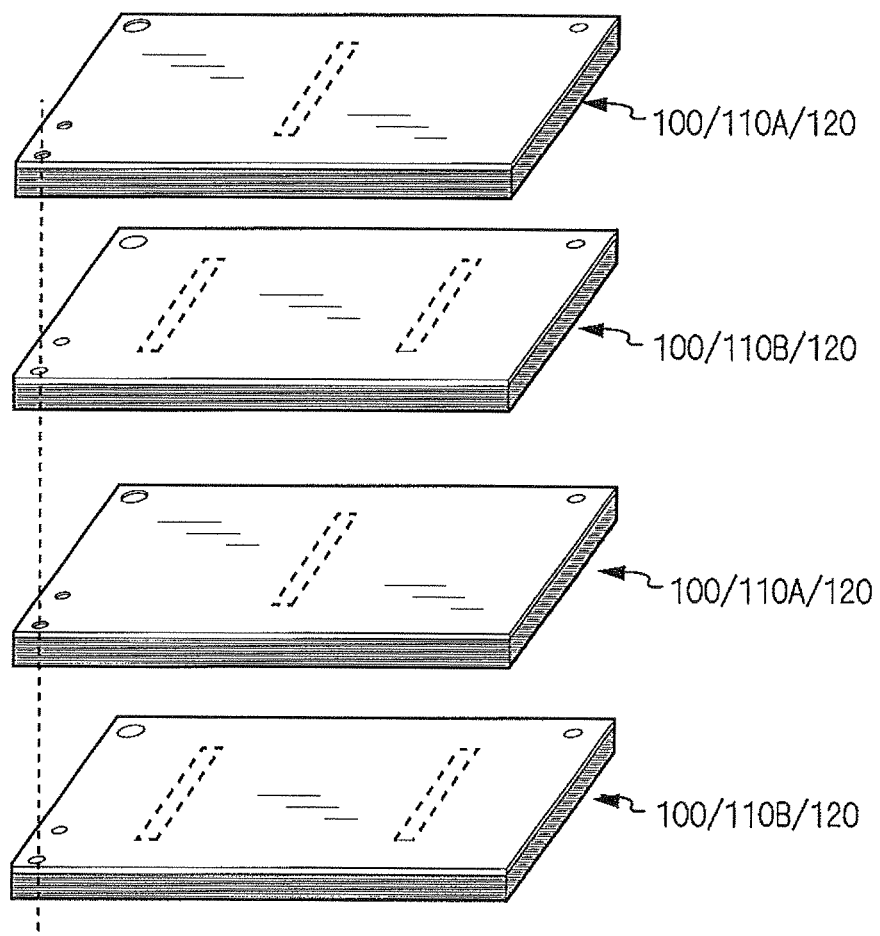
FIG. 3A is a perspective view for explaining a laminating step performed after the step shown in FIG. 2F.
Figure 3B:
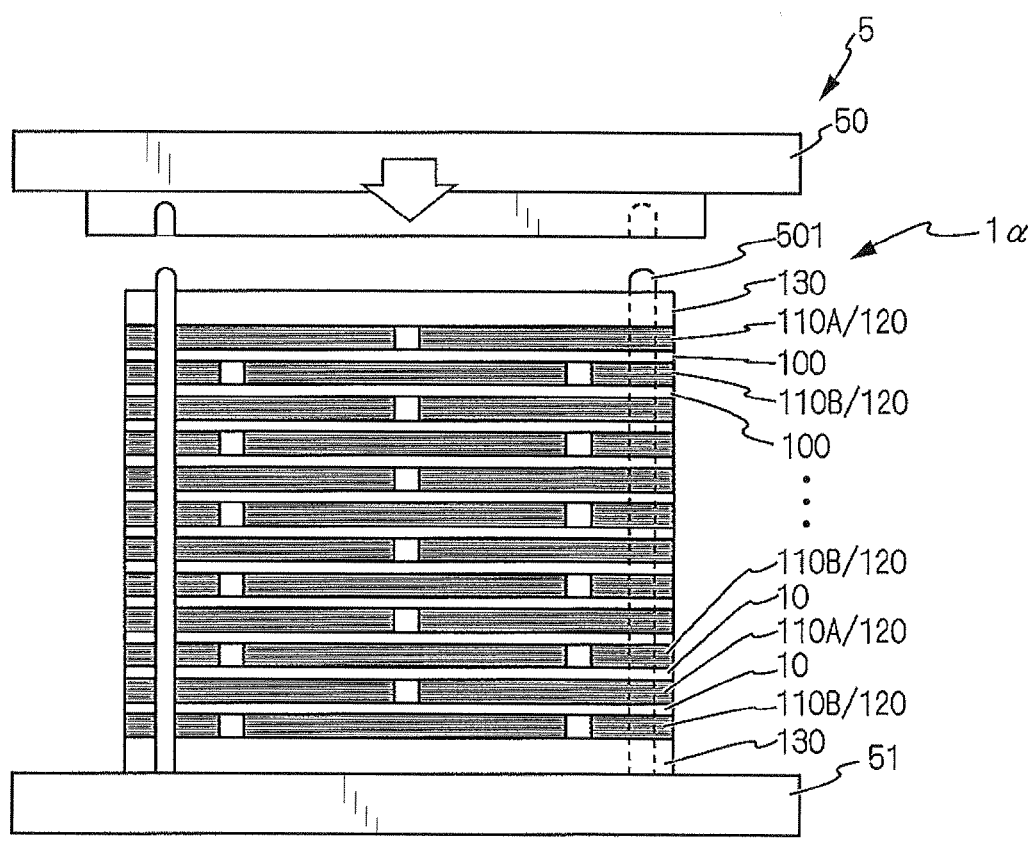
FIG. 3B is a cross-sectional view of the lamination obtained after the step shown in FIG. 3A, which is mounted on a laminating mold.

Next, as shown in FIG. 3A, a plurality of the first laminated sheets 100/110A/120 and a plurality of the second laminated sheets 100/110B/120 are laminated alternately. By repeating the above work, an electrode layer laminated body set 1α (may be referred to as the laminated body set 1α hereinafter) including 10 to 20 layers of the first and second laminated sheets 100/110A/120 and 100/110B/12 are obtained. More specifically, as shown in FIG. 3B, the first laminated sheets 100/110A/120 and the second laminated sheets 100/110B/120 are laminated alternately in 10 to 20 layers. Thereafter, a terminal insulating layer sheet 130 is heat-pressure bonded to each of the upper and lower surfaces of this lamination using a bonding die 5 to complete the electrode layer laminated body set 1α. In this embodiment, the bonding die 5 is a uniaxial pressing die. However, the bonding die 5 may be an HIP die (hot isostatic pressing die) or CIP die (cold isostatic pressing die).

Figure 4:
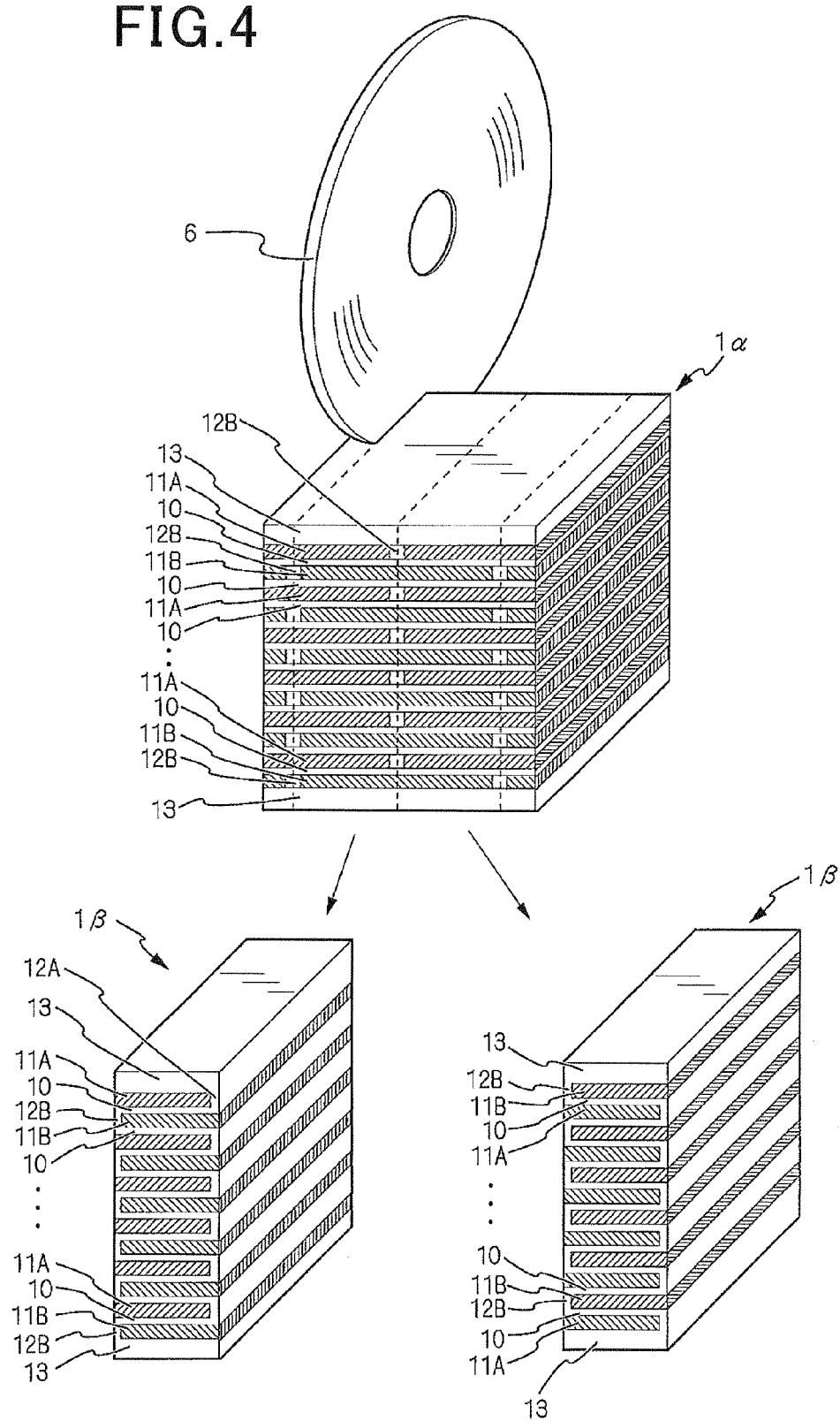
FIG. 4 is a perspective view for explaining a step of cutting out an electrode layer laminated body set performed after the step shown FIG. 3B.
Figure 5A:
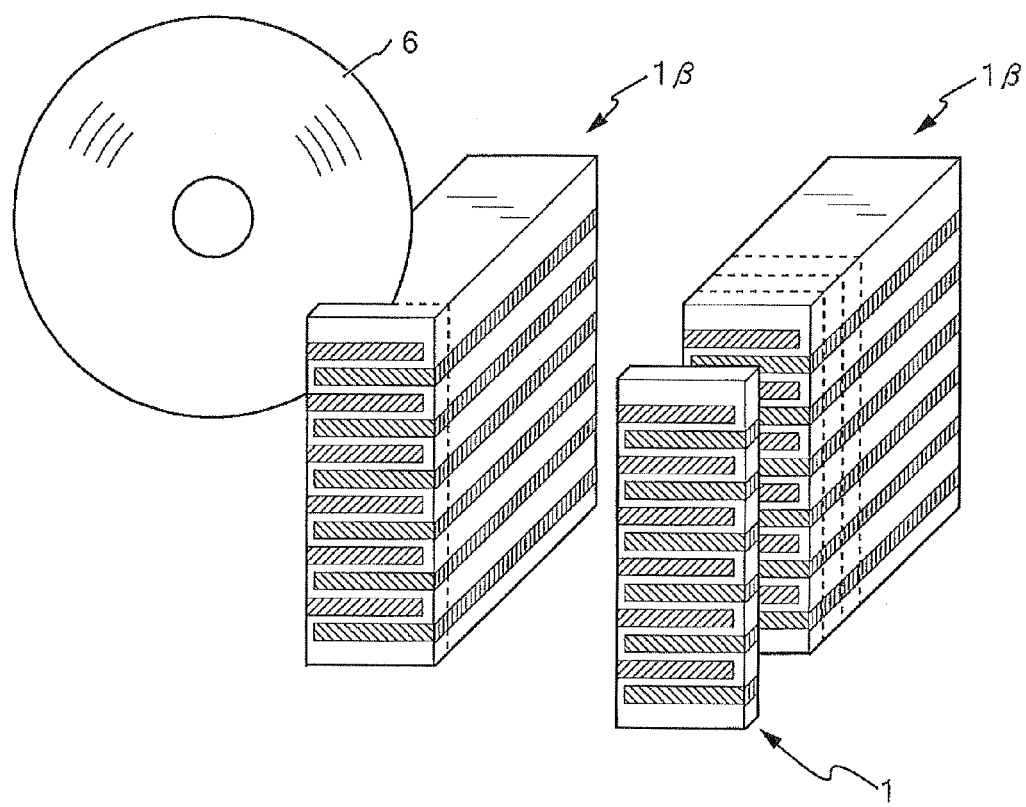
FIG. 5A is a perspective view for explaining a step of cutting out an electrode layer laminated body performed after the step shown in FIG. 4.

The obtained laminated body set 1α is dried or baked. Thereafter, the laminated body set 1α is cut into plural pieces using a dicing saw or the like as shown in FIGS. 4 and 5A. Incidentally, as shown in FIG. 4, a primary processed laminated body 1β obtained by dividing the laminated body set 1alph into two pieces has a symmetrical structure. Accordingly, the laminated bodies 1 can be cut out by evenly cutting each primary processed laminated body 1β into plural pieces. When the laminated body 1 has the dimensions of 20 mm ($W_1$)×5 mm ($L_1$)×0.5 mm ($T_1$), if the single laminated body set 1α is formed to the dimensions of 60 mm ($W_1$ direction)×5 mm ($L_1$ direction)×30 mm ($T_1$ direction), it is possible to cut the single laminated body set 1α into about 100 laminated bodies 1. Hence, according to this embodiment, the laminated body 1 can be manufactured with a high production efficiency. The laminated body 1 may be polished at its detection surface and mounting surface opposite to the detection surface after being cut out.

Figure 5B:
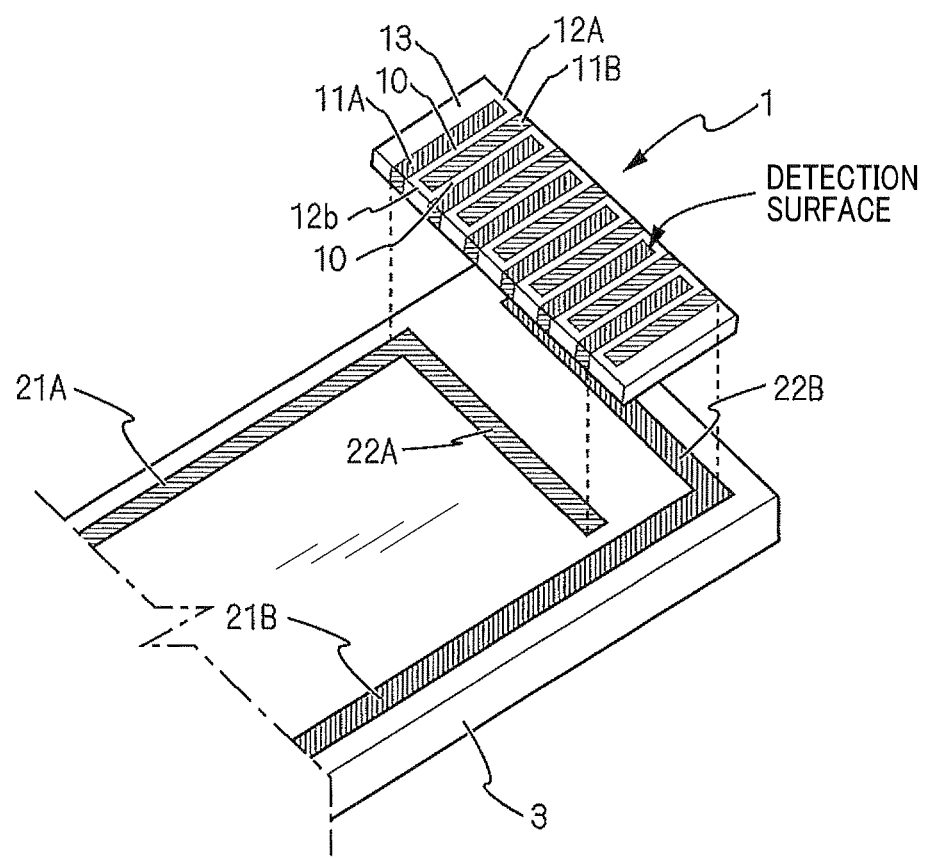
FIG. 5B is a perspective view for explaining a detection part mounting step performed after the step shown in FIG. 5B.
Figure 6A:
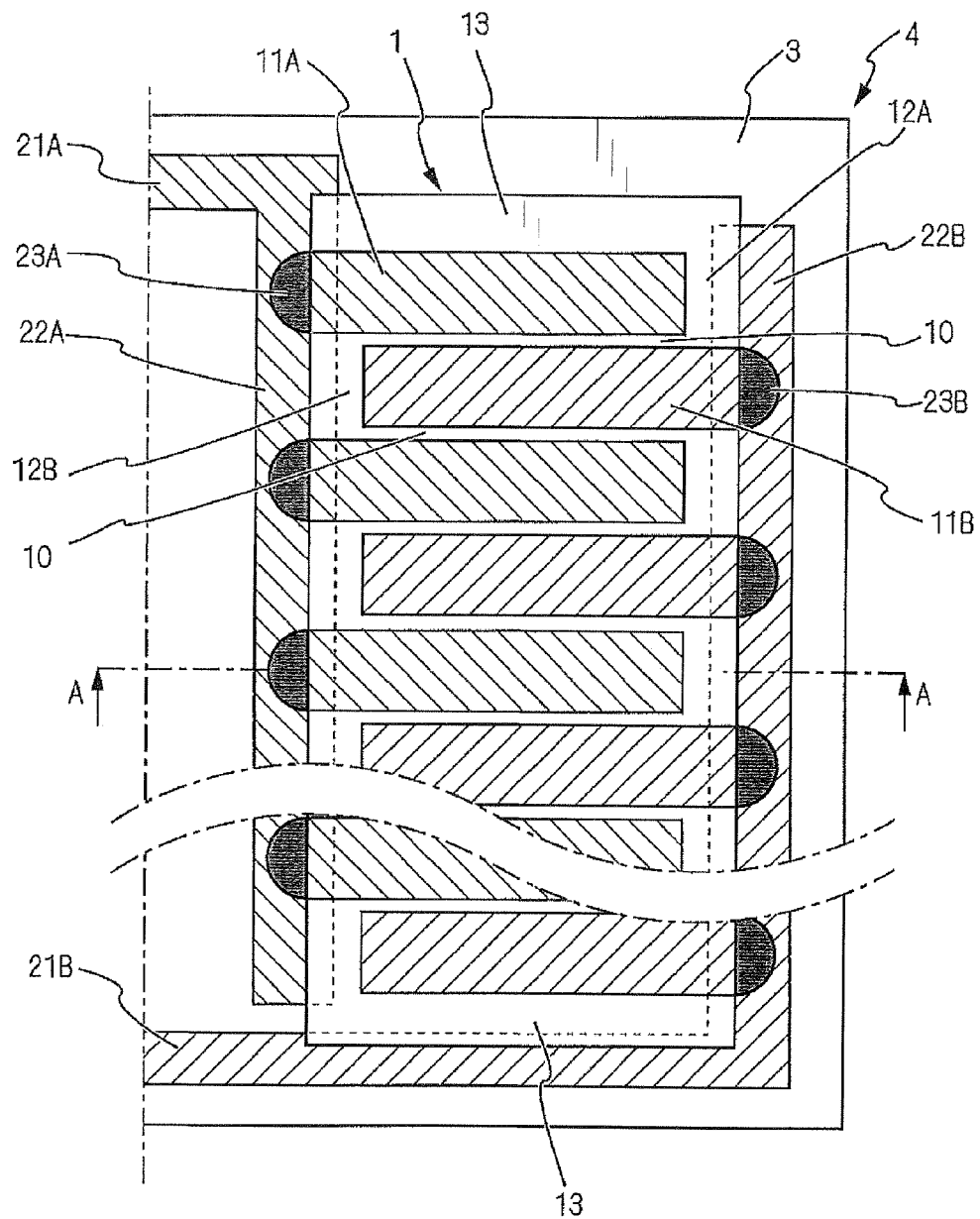
FIG. 6A is a plan view showing the electrode layer laminated body of the first embodiment in the mounted state.
Figure 6B:
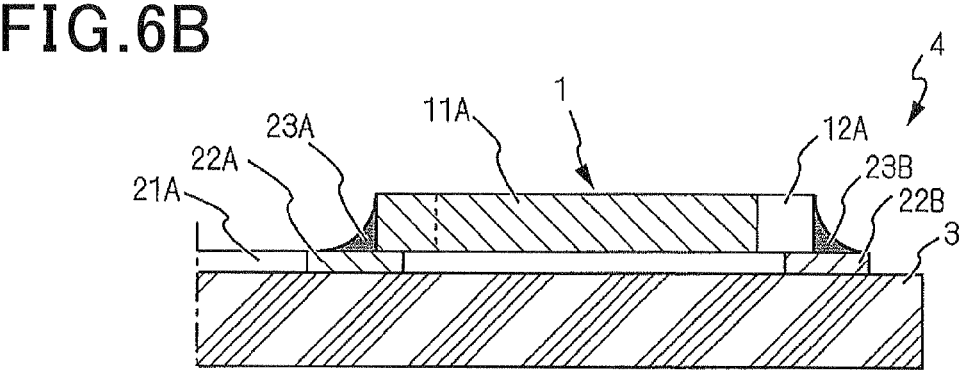
FIG. 6B is a cross-sectional view of FIG. 6A taken along line A-A.

As shown in FIG. 5B, the first and second lead portions 21A and 21B, and the first and second land portions 22A and 22B are formed on the surface of the insulating substrate 3 by a screen printing method or the like, and the laminated body 1 is mounted on the insulating substrate 3 to complete the PM detection element 4. As shown in FIGS. 6A and 6B, the first and second junction portions 23A and 23B are formed by soldering or brazing to connect the end of the first electrode layer 11A to the first land portion 22A, and connect the end of the second electrode layer 11B to the second land portion 22B, so that there are formed a pair of the comb-shaped electrodes in which the cross section of each first electrode layers 11A and the cross section of each second electrode layer 11B face each other across from the cross section of the intermediate insulating layer 10, and the first and second electrode layers 11A and 11B are separated into right and left alternately to be connected to the first land portion 22A and the second land portion 22B, respectively one of which is connected to the outside. As shown in FIGS. 6A and 6B, the first end-portion insulating layers 12A and the second end-portion insulating layers 12B serve to prevent the first electrode layers 11A and the second electrode layers 11B from being erroneously connected to the wrong land portions.

Figure 7A:
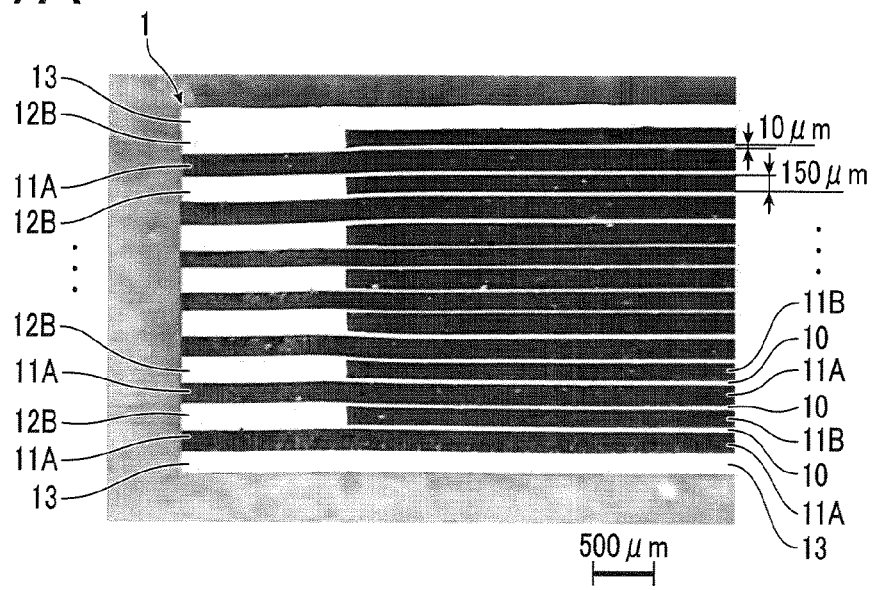
FIG. 7A is a photograph of the electrode layer laminated body of the first embodiment.

FIG. 7A is a photograph showing the detection surface of an example of the laminated body 1. In this example, the layer thickness $T_{INS}$ of the intermediate insulating layer 10 is 10 μm, and the layer thickness $T_{EL}$ of the first and second electrode layers 11A and 11B is 150 μm. However, the inventors have found through various tests that the intermediate insulating layer 10 can be formed to any thickness in a range from 3 μm to 20 μm with a high degree of accuracy, and the first and second electrode layers 11A and 11B can be formed to any thickness in a range from 50 μm to 500 μm with a high degree of accuracy.

Figure 7B:
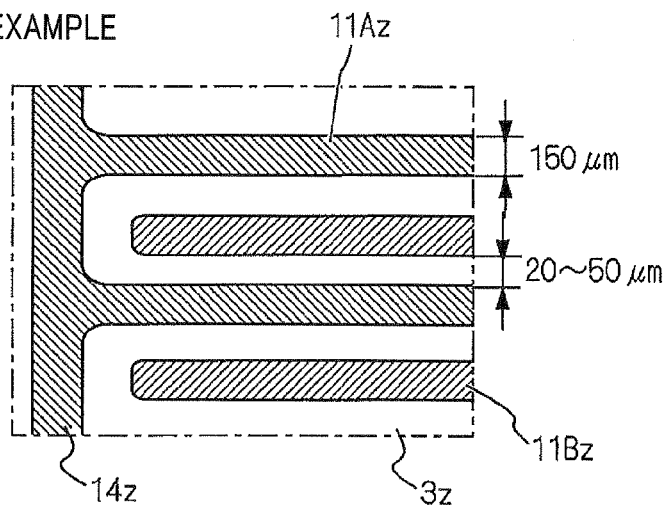
FIG. 7B is a plan view of a comb-shaped electrode as a comparative example formed using a common thick film printing method.
Figure 7C:
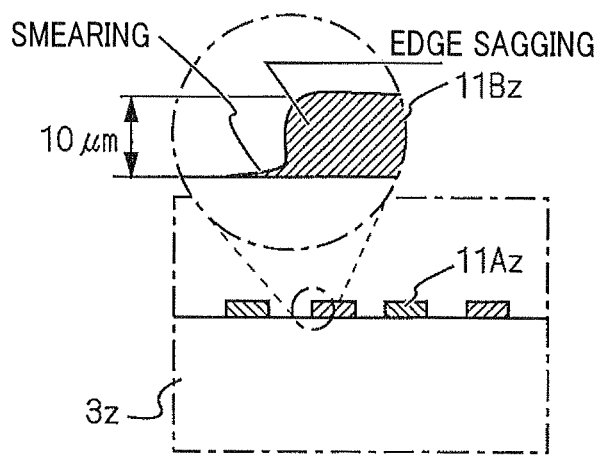
FIG. 7C is a cross-sectional view of FIG. 7B.

FIGS. 7B and 7C show, as an comparative example, comb-shaped detection electrodes 11Az and 11Bz formed by a common thick film printing method. In this comparative example, it is extremely difficult to print-form the detection electrodes located opposite to each other with a distance shorter than 20 μm. Furthermore, as shown in FIG. 7C in a magnified manner, it is not possible to avoid smearing of the edges of the detection electrodes 11Az and 11Bz on the surface of the substrate 3z, and edge sagging due to surface tension. In addition, variation of distance between the detection electrodes is large, because the edges of the detection electrodes are likely to be formed with fine unevenness or fading in the print squeegee direction. On the other hand, in the laminated body 1 of this embodiment, since the cross-sectional surfaces of the electrode layer sheet 110, the end-portion insulating layer 120 and the intermediate insulating layer 100 having been cut out using dies are used as the detection surface, the shapes of the first and second electrode layers 11A and 11B are very sharp, and accordingly the inter-electrode distance is kept constant quite accurately by the layer thickness $t_{INS}$ in the cross-sectional direction of the intermediate insulating layer 10.

Figure 8A:
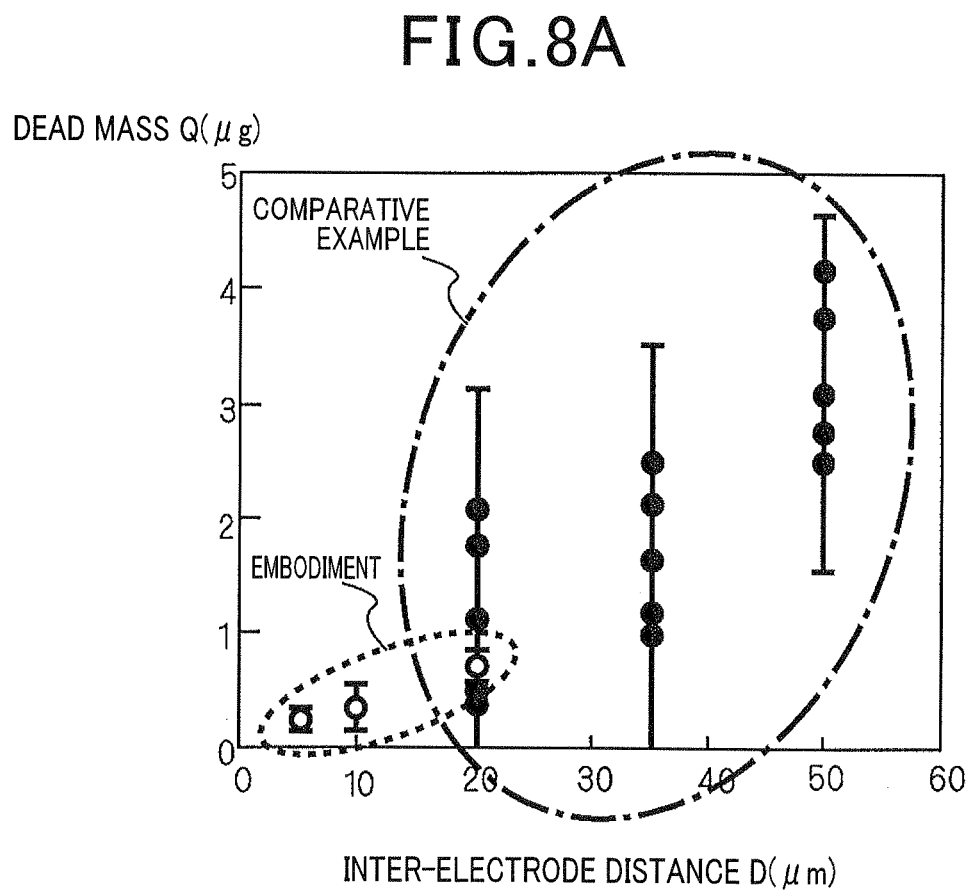
FIG. 8A is a diagram for explaining advantages of the invention regarding a dead mass while referring to the comparative example.

Next, advantages of the above describe embodiment are explained with reference to FIGS. 8A and 8B. FIG. 8A shows variation of the dead mass Q (μg) of each of five samples of a comparative example which include detection electrodes formed by a common thick film printing method when the distance D between the adjacent detection electrodes is changed in a range from 20 μm to 50 μm, and shows variation of the dead mass Q (μg) of each of five samples of the above embodiment of the invention when the distance D between the adjacent detection electrodes is changed in a range from 5 μm to 20 μm. FIG. 8B shows the coefficient of variation CV (=100 σ/μ (%)) calculated from the average (μ) and the standard deviation (σ) of the n (=5) samples for each of comparative example and the embodiment of the invention.

As seen from FIGS. 8A and 8B, the dead mass and its individual difference of the embodiment of the invention are far smaller than those of the comparative example. This is not only because the distance D between the detection electrodes is small in the embodiment, but also because since the cross-sectional surface in the laminated direction of the laminated body 1 is used as the detection surface, and the detection surface is completely planar, PM particles of nanometer size are arranged on the detection surface in a planar manner, and the electrical characteristic such as resistance, capacitance and impedance between the detection electrodes varies linearly in accordance with the number of the PM particles. In contrast, when the comb-shaped electrodes 11Az and 11Bz are print-formed on the surface of the conventional insulating substrate 3z, they have a solid structure having a film thickness of the order of 10 μm, and PM particulates collected in the detection electrodes are arranged sterically. As a result, not only the dead mass increases with the increase of the distance D between the detection electrodes, but also there are infinite number of variations of the arrangement of the PM particles enabling detection of the electrical characteristic, which causes the individual difference to increase.

Figure 9A:
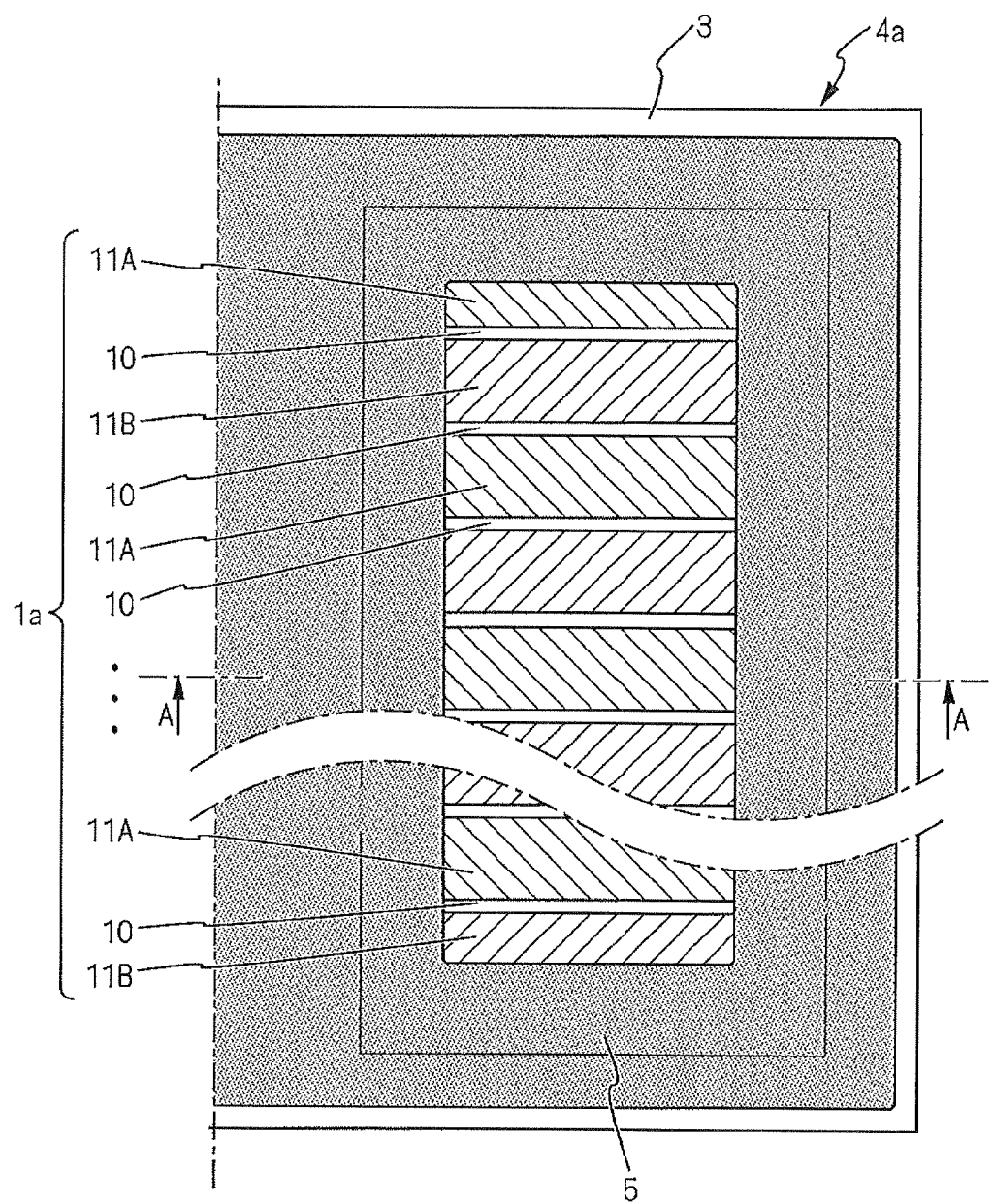
FIG. 9A is a plan view showing a major part of an electrode layer laminated body of a PM detection element according to a second embodiment of the invention.
Figure 9B:
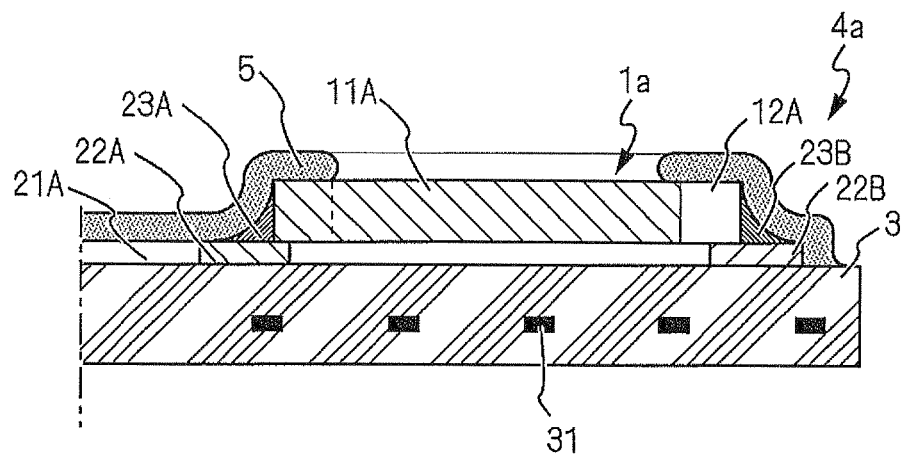
FIG. 9B is a cross-sectional view of FIG. 9A taken along line A-A.

Next, a PM detection element 4a according to a second embodiment is described with reference to FIGS. 9A and 9B. Incidentally, components of embodiments described hereinafter, which are the same as those of the first embodiment are indicated by the same reference numerals or letters, and explanations thereof are omitted. Components of the embodiments described hereinafter which are different from their equivalents in the first embodiment are identified by adding an alphabet to their reference numerals. The PM detection element 4a differs from the PM detection element 4 of the first embodiment in that a part exposed to the measured gas of a laminated body 1a is covered by a protection layer 5 except the detection surface in order to prevent malfunction due to PM adhered to this exposed part of the laminated body 1.

The protection layer 5 is made of a heat-resistant material such as heat-resistant glass or alumina. The protection layer 5 can be formed by a thick printing method, slurry applying method, or a green sheet laminating method. The PM detection element 4a of the second element is exposed to the outside from an opening 51 of the protection layer 5 only at its portion in which the first electrode layers 11A, the second electrode layers 11B and the intermediate insulating layers 10 are arranged in parallel, and the other portion is covered by a shield layer 50 of the protection layer 5. Accordingly, the second embodiment provides, in addition to the advantages provided by the first embodiment, an advantage that only the electric field generated uniformly between the first electrode layers 11A and the second electrode layers 11B acts on the PM suspending in the measured gas, and reduces uneven distribution of the PM collected on the surface of the laminated body la, as a result of which the detection accuracy is further increased. Incidentally, the protection layer 5 can be provided in any of embodiments described below.

Next, a laminated body 1b used in a PM detection element 4b according to a third embodiment of the invention and a method of manufacturing the laminated body 1b are described with reference to FIGS. 10A and 10B. In the above embodiments, the first electrode layers 11A and the second electrode layers 11B are connected respectively to the first land portion 22A and the second land portion 22A at their ends outside the laminated body. Unlike in the above embodiments, in the third embodiment, first and second common electrode layers 14A and 14B to be connected respectively to the first and second electrode layers 11A and 11B are formed by a common electrode forming step. The third embodiment provides, in addition to the advantages provided by the above embodiments, an advantage that the first and second common electrode layers 14A and 14B disposed in different lateral directions of the laminated body 1b can be connected respectively to the first and second land portions 22A and 22B, and connection to the wrong land portions can be reliably prevented.

Figure 10A:
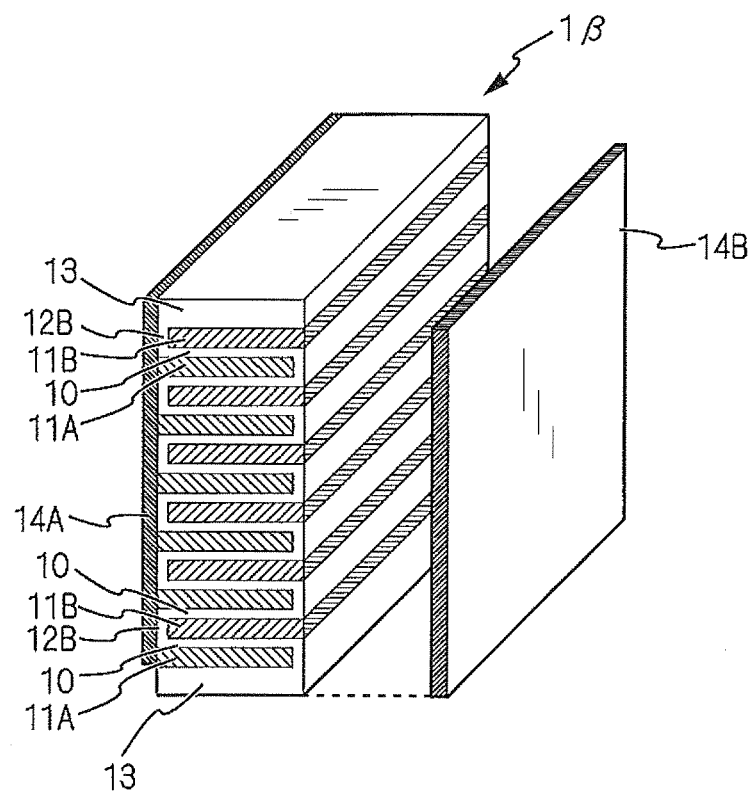
FIG. 10A is a perspective view for explaining a step of forming common electrodes included in a method of manufacturing a PM detection element according to a third embodiment of the invention.
Figure 10B:
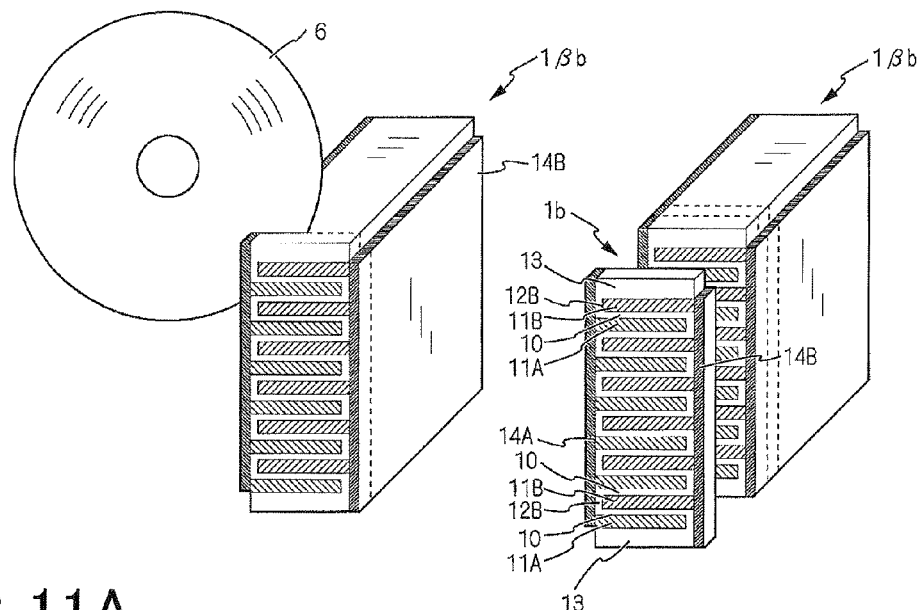
FIG. 10B is a perspective view for explaining a step of cutting out an electrode layer laminated body performed after the step shown in FIG. 10A.

As shown in FIG. 10A, the first and second common electrode layers 14A and 14B having a plate-like shape are formed on both lateral sides of the primary processed laminated body 1β by a thick film printing method or a green sheet applying method. The first and second common electrode layers 14A and 14B may be formed by sticking the electrode layer sheet 110 on the lateral side of the primary processed laminated body 1β from which the ends of one of the first and second electrode layers 11A and 11B are exposed, and thereafter baking them together. Alternatively, the first and second common electrode layers 14A and 14B may be formed by being print-formed on the lateral sides of the primary processed laminated body 1β using a conductive oxide material in a paste state, and thereafter being baked. FIG. 10B shows the primary processed laminated body 1β formed with the common electrode layers 14A and 14B by the above described way. As seen from FIG. 10B, by cutting the primary processed laminated body 1β formed with the common electrodes 14A and 14B to even thickness, the laminated body 1b integrally formed with the first and second common electrode layers 14A and 14B is obtained.

Next, a method of manufacturing a PM detection element 4c as a modification embodiment of the third embodiment is described with reference to FIGS. 11A to 11D, 12A, 12B and 13. In the third embodiment, the laminated body 1b is formed by after-processing the first and second common electrode layers 14A and 14B. In this modification embodiment, a common electrode embedding process for embedding a common electrode layer sheet 140 is performed during the laminating step to form a laminated body 1c having the same structure as the laminated body 1b and form the detection element 4c.

Figure 11A:
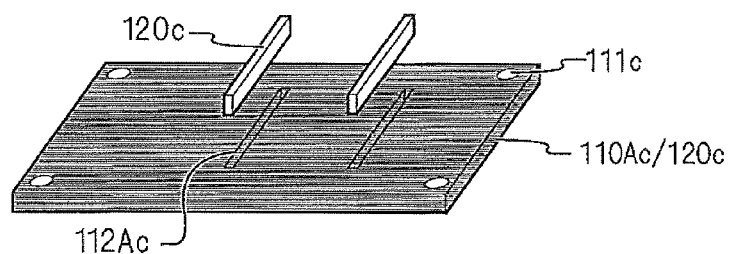
FIG. 11A is a perspective view for explaining a step of embedding an insulating layer included in a modification of the method of manufacturing the PM detection element according to the third embodiment of the invention.
Figure 11B:
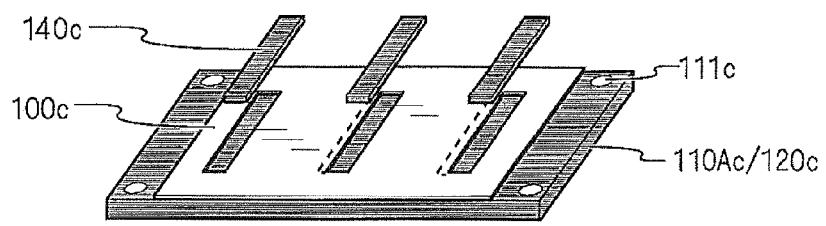
FIG. 11B is a perspective view for explaining a step of forming an intermediate insulating layer performed after the step shown in FIG. 11A.
Figure 11C:
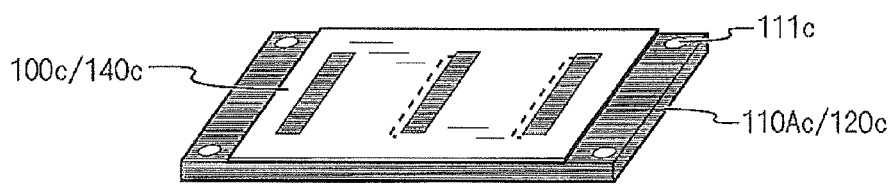
FIG. 11C is a perspective view of a first electrode layer green sheet formed with the intermediate insulating layer obtained after the step shown in 11B.

In this modification embodiment, the end-portion insulating layer sheet 120c is embedded in the electrode layer sheet 110 as shown in FIG. 11A, and also the common electrode layer sheet 140 for forming common electrode layers 14Ac and 14Bc is embedded in the intermediate insulating layer sheet 100 as shown in FIG. 11C. Thereafter, these are laminated to form a first laminated sheet 100c/140c/110Ac/120c. In this modification embodiment, the electrode layer sheet 140 is embedded in the intermediate insulating layer sheet 100c/140c for pattern formation. However, the pattern formation may be made by printing the intermediate insulating layer 100c and common electrode layer 140c in an overlapped manner on the surface of the electrode layer sheet 110A/120 embedded with the end-portion insulating layer sheet 120 using a screen printing method.

Figure 11D:
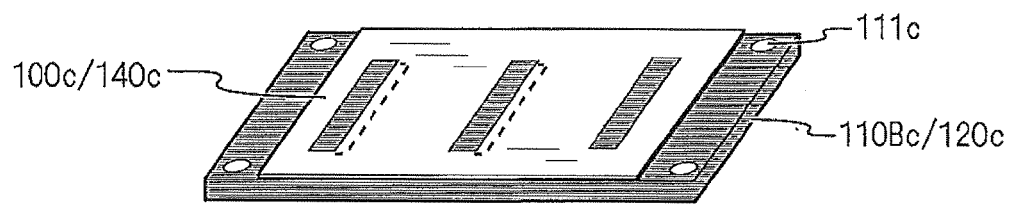
FIG. 11D is a perspective view of a second electrode layer green sheet obtained by rotating the first electrode layer green sheet shown in FIG. 11C by 180 degrees.

By rotating the first laminated sheet 100c/140c/110Ac/120c obtained by the above process by 180 degrees as shown in FIG. 11D, a second laminated sheet 100c/140c/110Bc/120c is obtained.

Figure 12A:
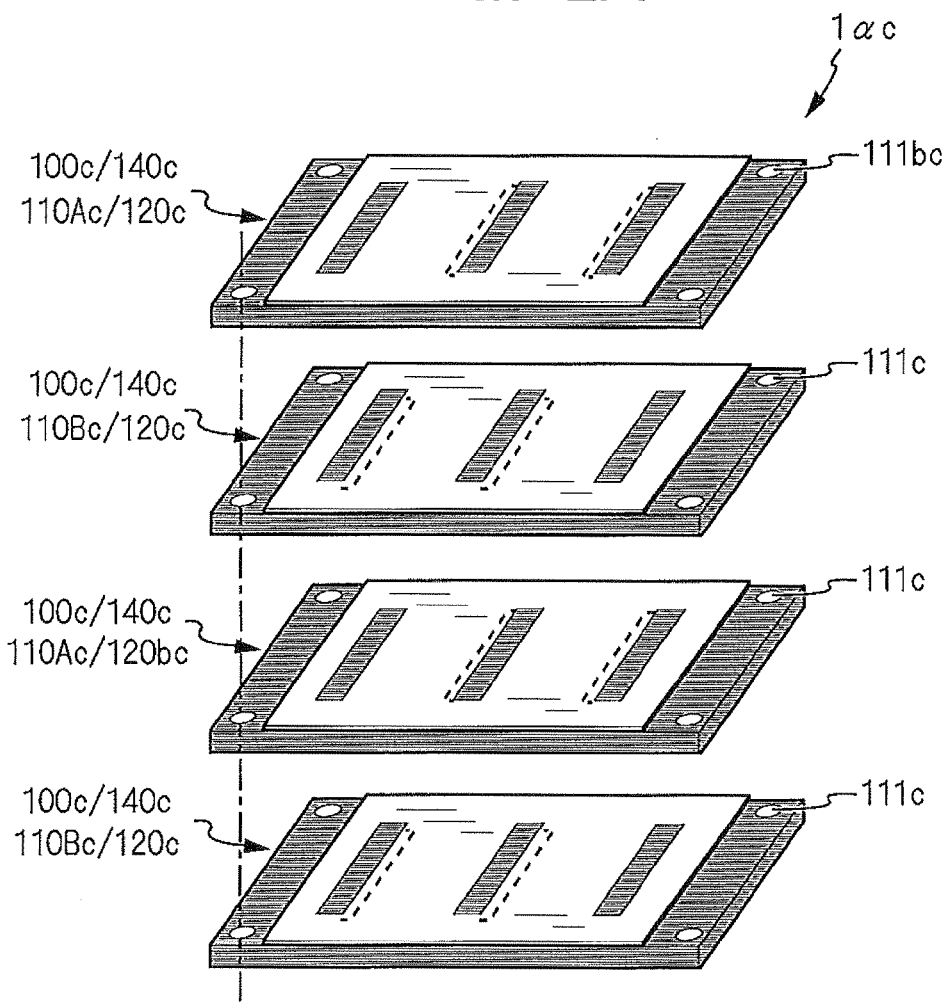
FIG. 12A is a perspective view for explaining a laminating step performed after the step shown in FIG. 11D.
Figure 12B:
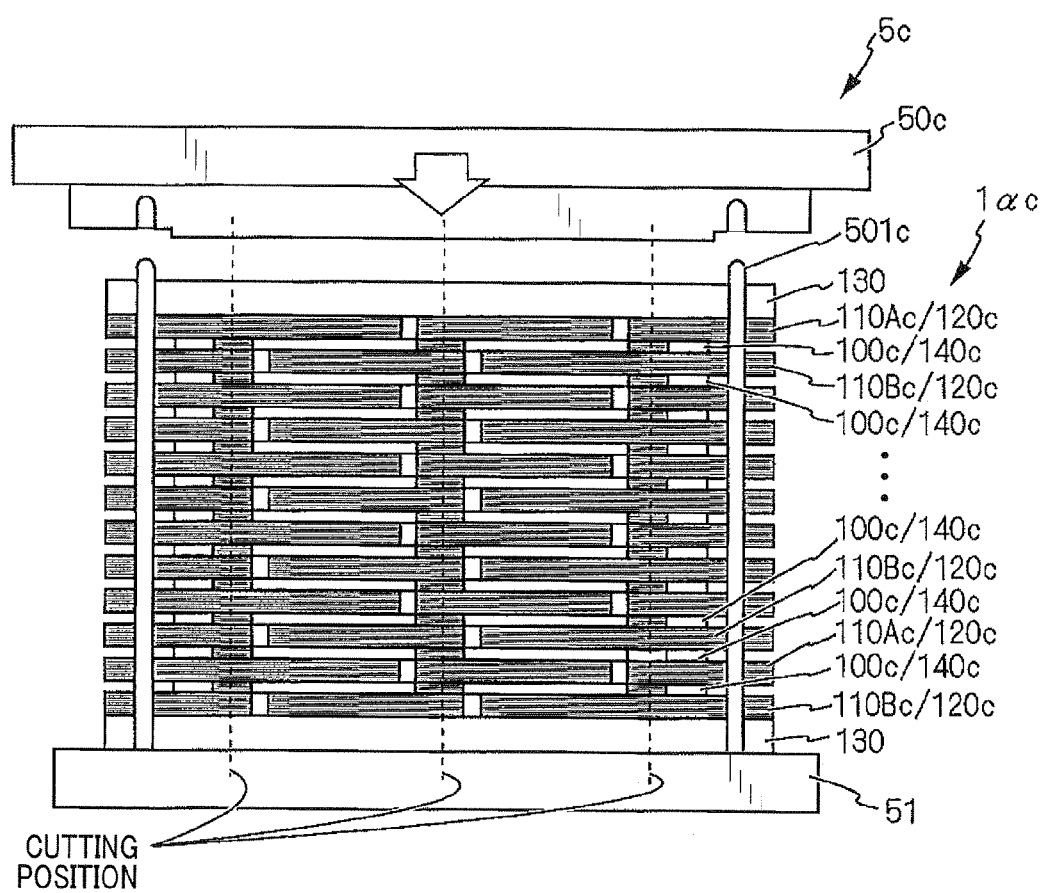
FIG. 12B is a cross-sectional view of the lamination obtained after the step shown in FIG. 12A, which is mounted on a laminating mold.
Figure 13:
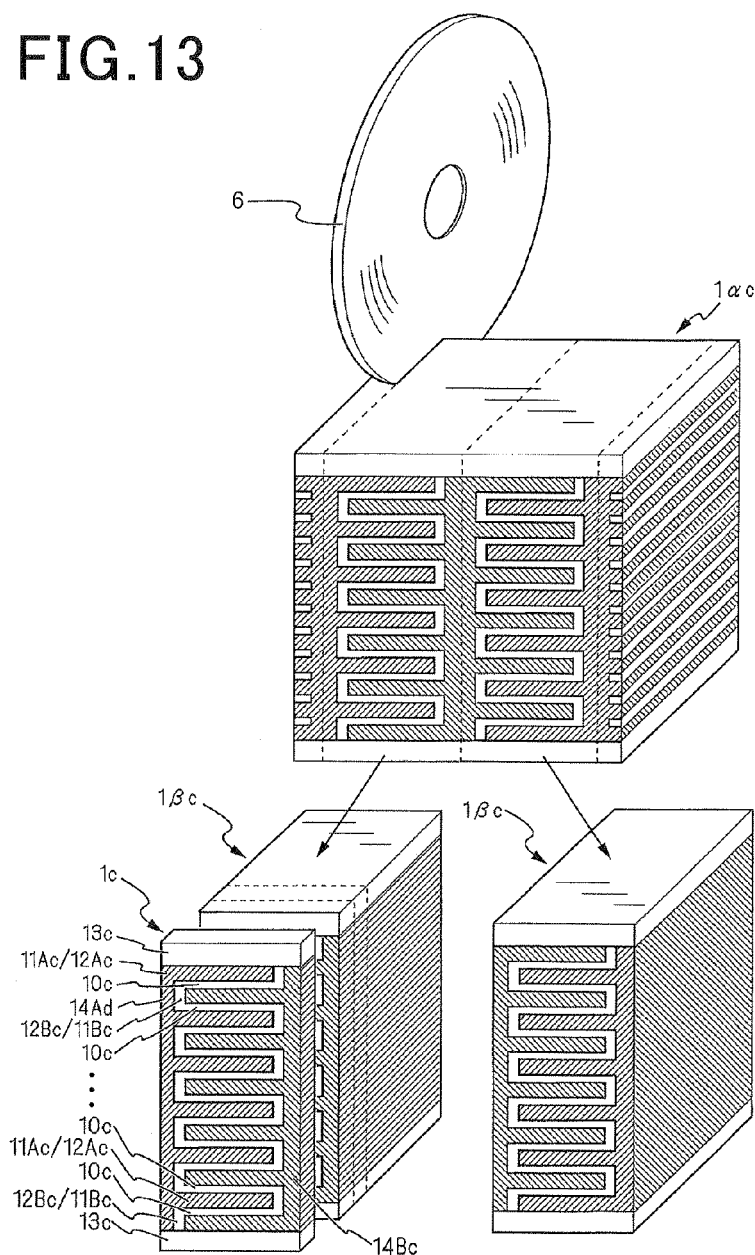
FIG. 13 is a perspective view for explaining a step of cutting out an electrode layer laminated body set performed after the step shown FIG. 12B.

Next, the first laminated sheets 100c/140c/110Ac/120c and the second laminated sheets 100c/140c/110Bc/120c are laminated in an alternating manner as shown in FIG. 12A, and thereafter disposed in a bonding die 5c to be heat-bonded as shown in FIG. 12B. As a result, an electrode layer laminated body set 1αc including the common electrode layers 140c formed therein is obtained.

Next, the electrode layer laminated body set 1αc is divided into two primary processed laminated bodies 1βc. Thus obtained primary processed laminated body 1βc is cut into pieces having the same thickness. According to this modification embodiment, it is possible to integrally form a pair of the comb-shaped electrodes opposite to each other with the intermediate insulating layers 10c disposed therebetween in which the first electrode layers 11A are connected to the first common electrode layer 14A formed along one lateral side of the laminated body 1c, the second electrode layers 11B are connected to the second common electrode layer 14B formed along the other lateral side.

Like the PM detection element 4 of the first embodiment, the PM detection element 4c of this modification embodiment is obtained by mounting the laminated body 1c to the first and second land portions 22A and 22B formed in the insulating substrate 3. At the time of the mounting, the first and second common electrode layers 14A and 14B are joined respectively to the first and second land portions 22A and 22B simply by soldering or the like. Accordingly, there is no concern that first and second common electrode layers 14A and 14B are erroneously connected to the second and first land portions 22B and 22A, respectively. In addition, since the first and second common electrode layers 14A and 14B can be joined respectively to the first and second land portions 22A and 22B wholly, the junction strength and the conduction reliability are high.

Next, a method of manufacturing a PM detection element 4d including a laminated body 1d as a modification embodiment of the first embodiment is described with reference to FIGS. 14A to 14D. In this modification embodiment, the laminated body 1d is the same in structure as the laminated body 1 of the first embodiment. This modification embodiment is partially different from the first embodiment in their manufacturing methods. In the first embodiment, the first laminated sheets 110A/120 and the second laminated sheets 110B/120 each including the end-portion insulating layer sheet 120 embedded therein are laminated alternately while interleaving the intermediate insulating layer sheets 100 therebetween.

Figure 14A:
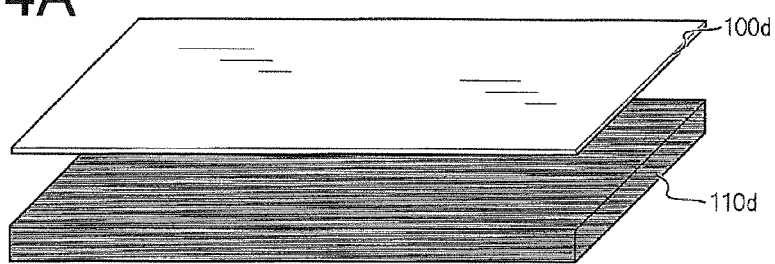
FIG. 14A is a perspective view for explaining a laminating step included in a modification of the method of manufacturing the PM detection element according to the first embodiment of the invention.
Figure 14B:
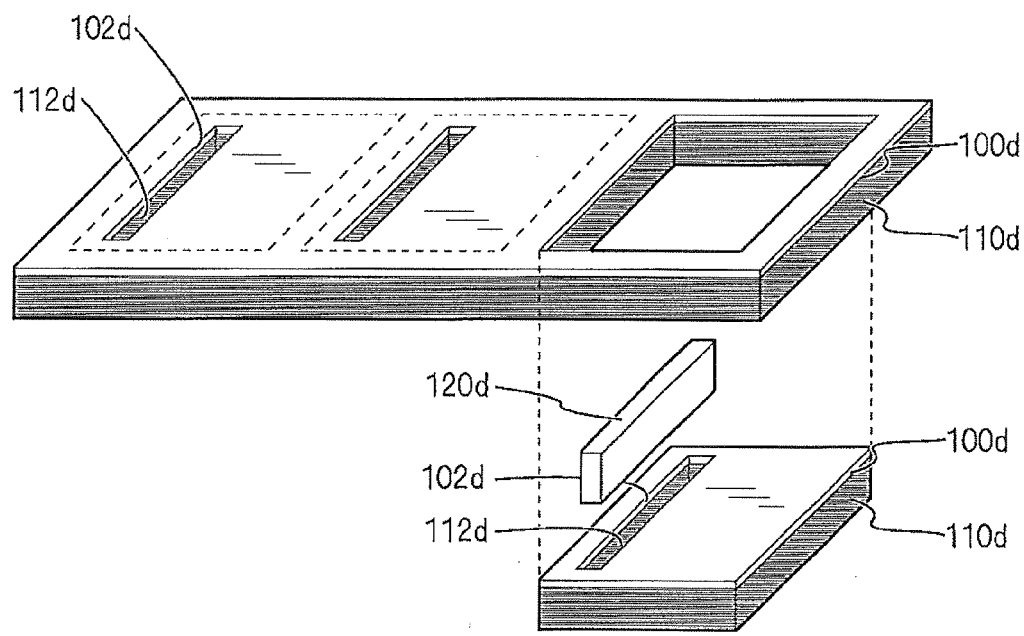
FIG. 14B is a perspective view for explaining a cutout step and an insulating layer embedding step performed after the step shown in FIG. 14A.
Figure 14C:
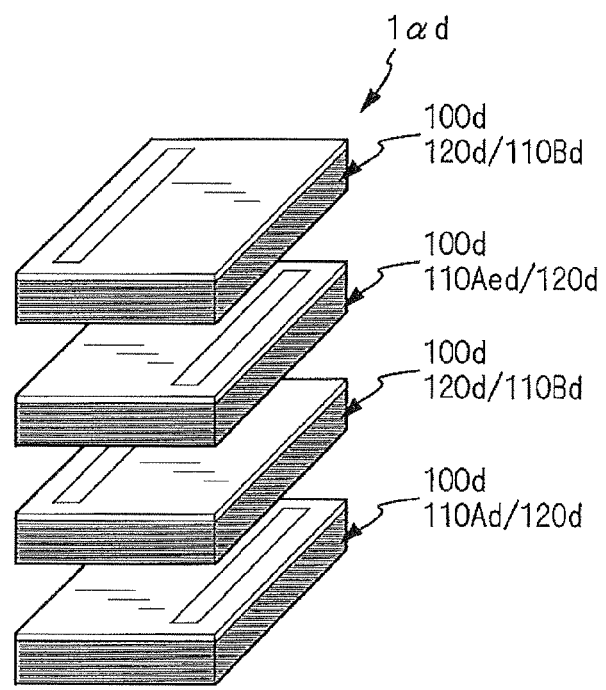
FIG. 14C is a perspective view for explaining a laminating step performed after the step shown in FIG. 14B.
Figure 14D:
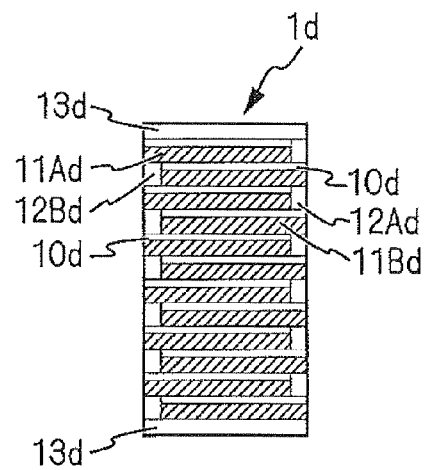
FIG. 14D is a plan view of an electrode layer laminated body obtained after the step shown in FIG. 14C.

Meanwhile, as shown in FIG. 14A, in this modification embodiment, the electrode layer sheet 110 and the intermediate insulating layer sheet 100 are laminated and bonded to each other as shown in FIG. 14B, and insulating layer embedding holes 102d and 112d are perforated jointly. Thereafter, the lamination of the electrode layer sheet 110 and the intermediate insulating layer sheet 100 is cut into even pieces, while embedding the end-portion insulating layer sheets 120d formed in the same thickness as this lamination in these holes, to thereby form a first laminated sheets 100d/120d/110Ad. Thereafter, the first laminated sheets 100d/120d/110Ad and the second laminated sheets 100d/120d/110Bd obtained by rotating the first laminated sheets by 180 degrees are laminated alternately, and are pressure-bonded to thereby form a laminated body set 1αd. By baking and cutting the laminated body set 1αd, a laminated body id shown in FIG. 14D is obtained. According to this modification embodiment, it is possible to from the laminated body set 1αd in which the first electrode layers 11Ad each of which is covered at its one end by the first end-portion insulating layer 120d and exposed at its other end in the lateral direction, and the second electrode layers 11Bd each of which is exposed at its one end in the opposite direction with the first electrode layers 11Ad and covered at its other end by the second end-portion insulating layer 120d are laminated alternately without causing positional deviation by forming the positioning holes 101 and 111 and using the bonding die 5. Like the foregoing embodiments, the laminated body 1d includes a terminal insulating layer 13d at each of the upper and lower terminal portions thereof. By mounting the laminated body 1 on the insulating substrate 3 formed with the electrode drawing layer 2 like the first embodiment, the PM detection element 4d is completed.

Figure 15A:
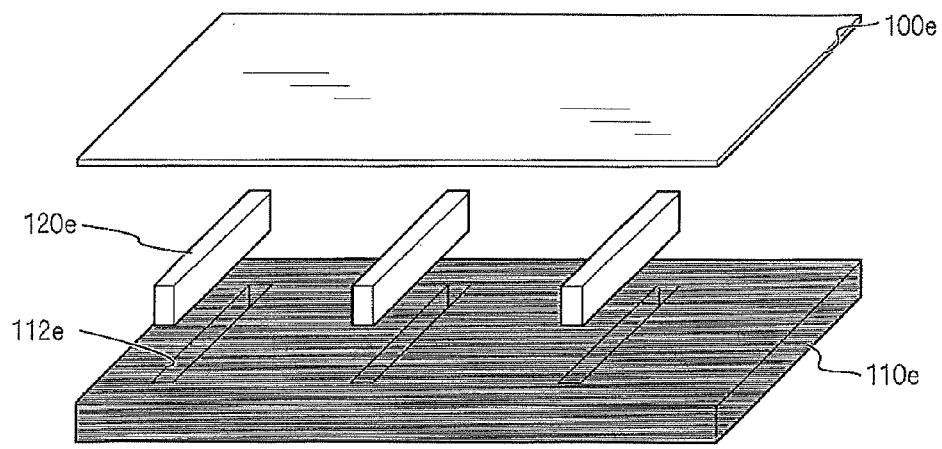
FIG. 15A is a perspective view for explaining an insulating layer embedding step and a laminating step included in another modification of the method of manufacturing the PM detection element according to the first embodiment of the invention.
Figure 15B:
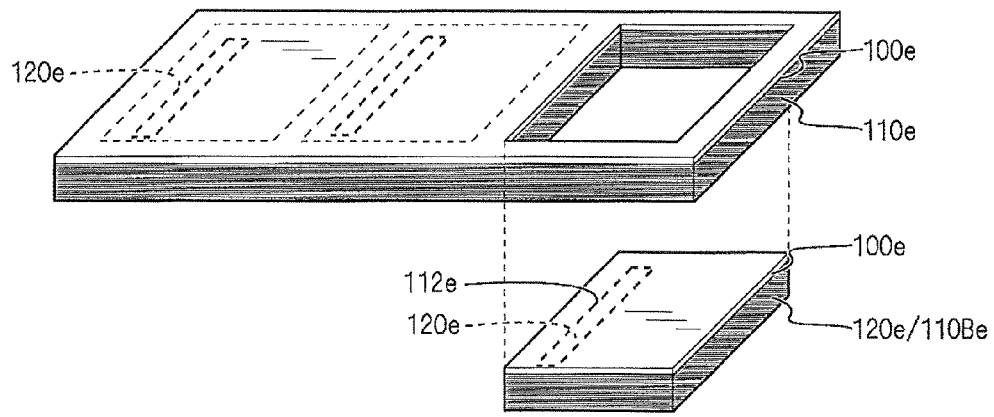
FIG. 15B is a cutout step performed after the steps shown in 15A.
Figure 15C:
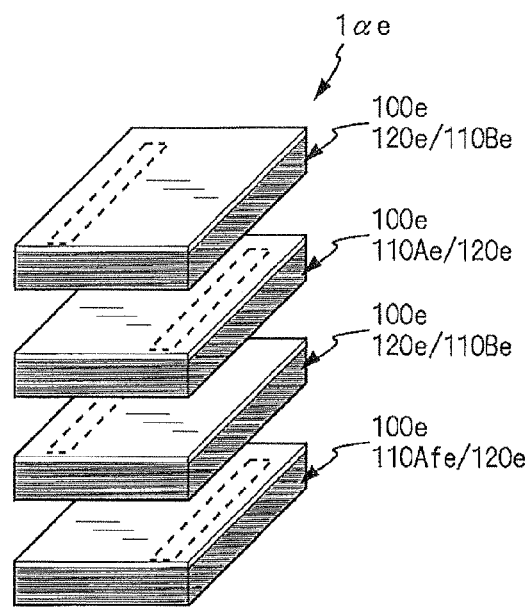
FIG. 15C is a perspective view for explaining a laminating step performed after the step shown in FIG. 15B.
Figure 15D:
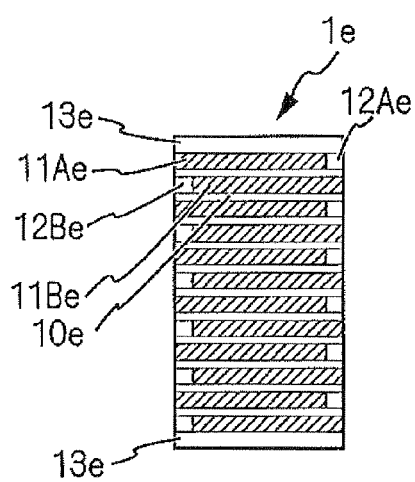
FIG. 15D is a plan view of an electrode layer laminated body obtained after the step shown in FIG. 15C.

Next, a method of manufacturing a PM detection element 4e including the laminated body 1d as another modification embodiment of the first embodiment is described with reference to FIGS. 15A to 15D. In the above described modification embodiment, the end-portion insulating layer sheets 120d are embedded in the lamination of the electrode layer sheet 110 and the intermediate insulating layer sheet 100. In this modification embodiment, as shown in FIG. 15A, only an electrode layer sheet 110e is embedded with end-portion insulating layer sheets 120e, and then laminated with an intermediate insulating layer sheet 100e. Thereafter, as shown in FIG. 15B, it is cut into even pieces to form first laminated layer sheets 100e/110Ae/120e. Thereafter, as shown in FIG. 15C, the first laminated layer sheets 100e/110Ae/120e and second laminated layer sheets 100e/120e/110Be obtained by rotating the first laminated layer sheets are laminated alternately. By baking and cutting this lamination in the same way as described above, a laminated body 1e which is substantially the same in structure as the laminated body 1 of the first embodiment is obtained. By mounting the laminated body 1e on the insulating substrate 3 formed with the electrode drawing layer, the PM detection element 4e is completed.

Figure 16A:
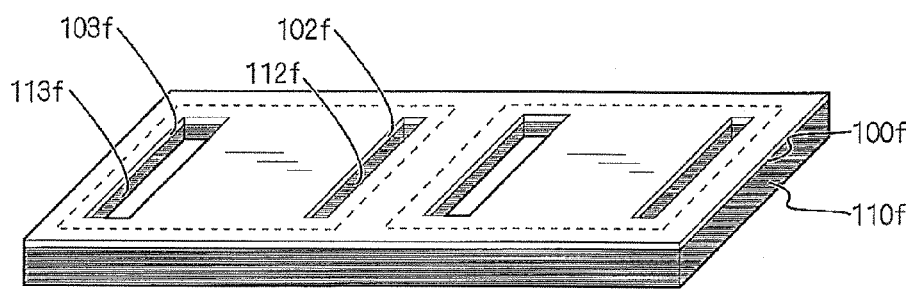
FIG. 16A is a perspective view for explaining a laminating step included in a modification of the method of manufacturing the PM detection element according to the third embodiment of the invention.
Figure 16B:
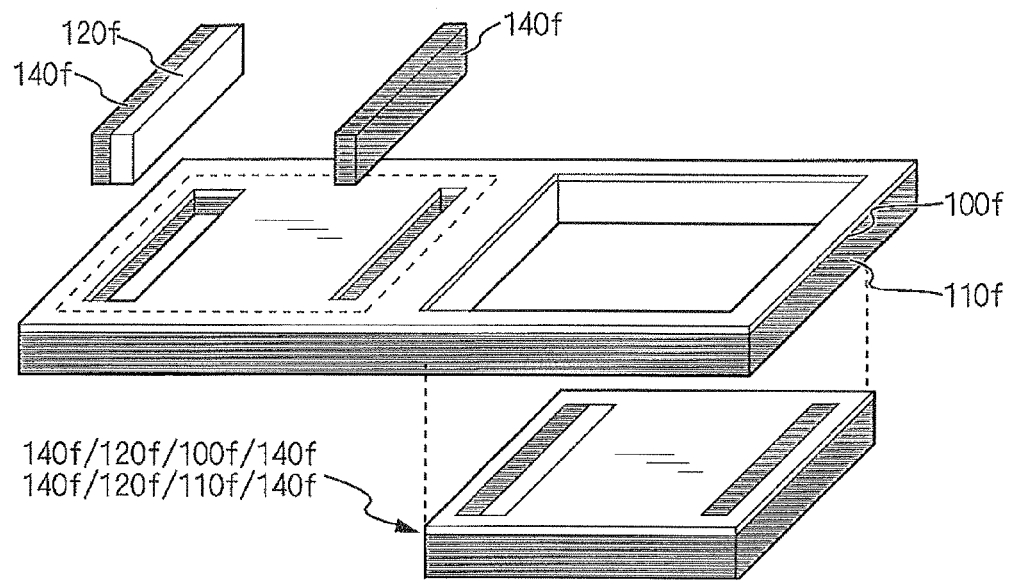
FIG. 16B is a perspective view for explaining a step of cutting out an electrode layer laminated body performed after step shown in FIG. 16A.
Figure 16C:
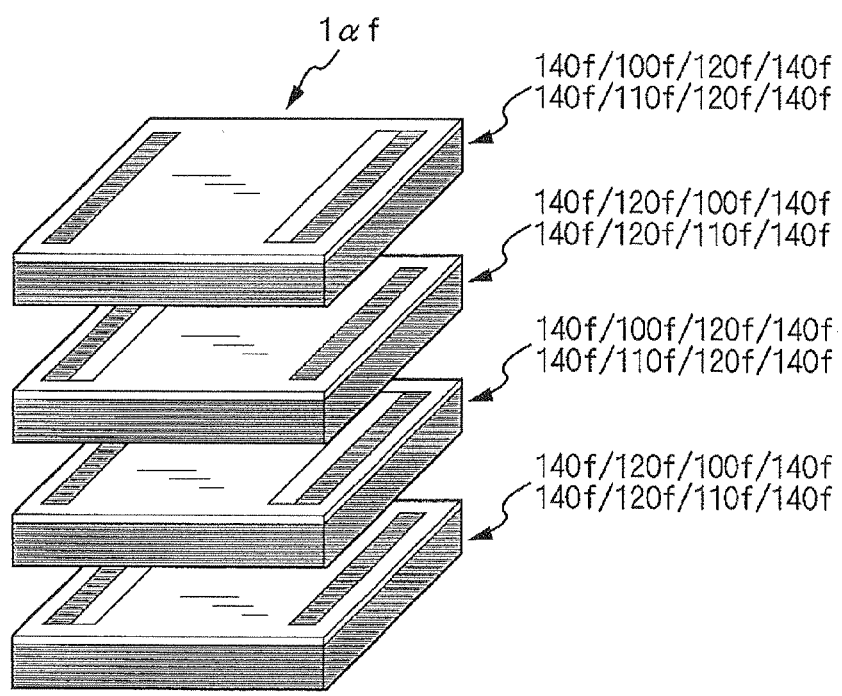
FIG. 16C is a perspective view for explaining a mounting step performed after the step shown in FIG. 16B.
Figure 16D:
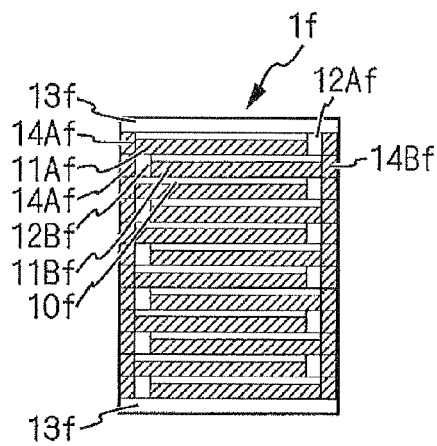
FIG. 16D is a plan view of the electrode layer laminated body obtained after the step shown in FIG. 16B.
Figure 17A:
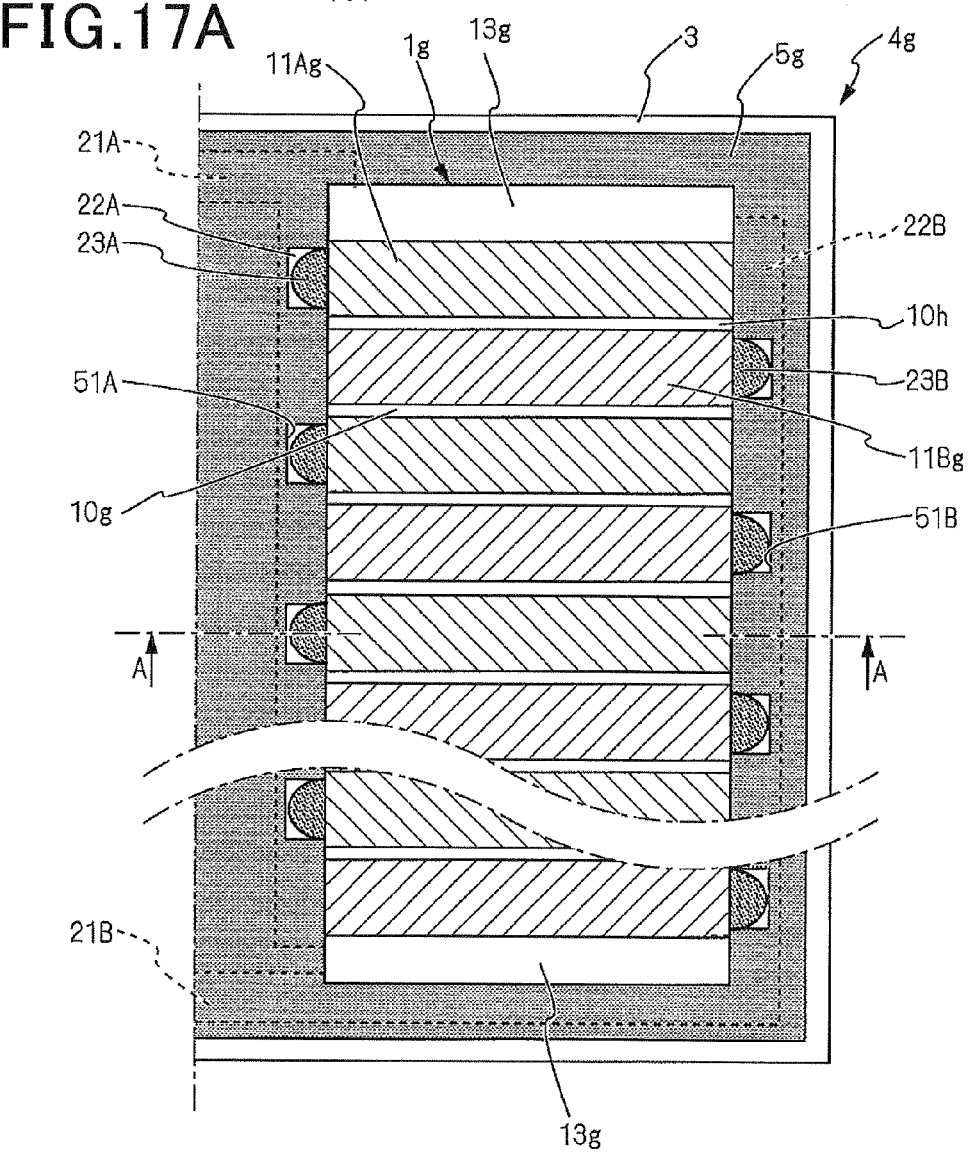
FIG. 17A is a plan view showing a major part of an electrode layer laminated body of a PM detection element according to a fourth embodiment of the invention.
Figure 17B:
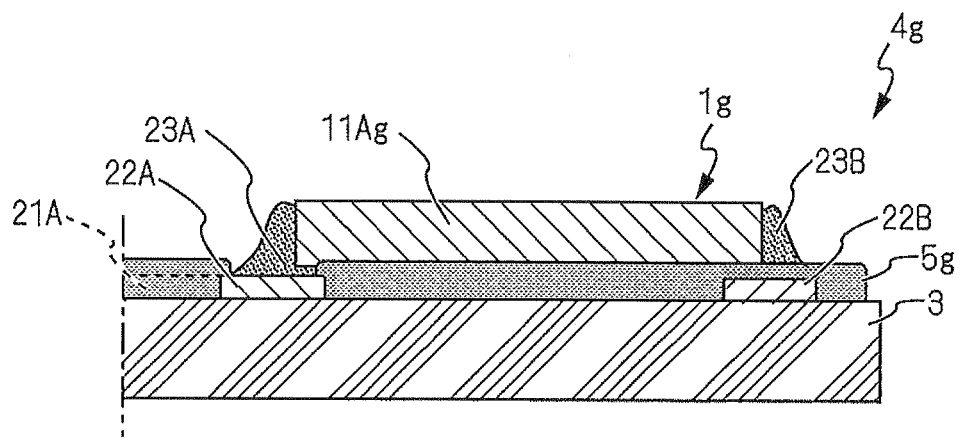
FIG. 17B is a cross-sectional view of FIG. 17A taken along line A-A.

Next, a method of manufacturing a PM detection element 4f including a laminated body 1f as a modification embodiment of the third embodiment is described with reference to FIGS. 16A to 16D. The method manufacturing the laminated body 1f of this modification embodiment which is substantially the same as the laminated bodies 1b and 1c of the third embodiment is partially different from the method of manufacturing the laminated bodies 1b and 1c. In this modification embodiment, after the electrode layer sheet 110 and the intermediate insulating sheet 100 are laminated on each other, electrode layer embedding holes 102f and 112f and electrode layer/insulating layer embedding holes 103f and 113f are perforated in this lamination as shown in FIG. 16A. Subsequently, as shown in FIG. 16B, a common electrode layer sheet 140f is embedded in each of the electrode layer embedding holes 102f and 112f, and the common electrode layer sheet 140f and an end-portion insulating layer sheet 120f are embedded together in each of the electrode layer/insulating layer embedding holes 103f and 113f. Next, this lamination is cut into even pieces. Thereafter, resultant first laminated sheets 140f/100f/120f/140f/140f/110f/120f/110f/ 140f and second laminated sheets 140f/120f/100f/140f/140f/ 110f/120f/140f obtained by rotating the first laminated sheets by 180 degrees are laminated alternately, and then are subjected to a pressure-bonding process, a baking process and a cutout process. As a result, the laminated body 1f shown in FIG. 16D is obtained. The obtained laminated body 1f is mounted on the insulating substrate 3 formed with the electrode drawing layer 2 to complete the PM detection element 4f which is substantially the same in structure as the detection elements 1b and is of the third embodiment.

Next, a PM detection element 4g including a laminated body 1g according to a fourth embodiment of the invention, and a method of manufacturing the PM detection element 4g is described with reference to FIGS. 17A, 17B, 18A, 18B, 18C and 18D. In the above embodiments, in order to expose one ends of the first electrode layers 11A and one ends of the second electrode layers 11B opposite to each other across from the intermediate insulating layers 10 in an alternate manner for the purpose of preventing a short-circuit between the first and second electrode layers 11A and 12B, the other ends of the first electrode layer 11A are covered by the first end-portion insulating layers 12A, the other ends of the second electrode layers 11B are covered by the second end-portion insulating layers 12B, and the first electrode layers 11A and the second electrode layers 11B exposed from the opposite lateral sides of the laminated body 1 are connected respectively to the first land portion 22A and the second land portion 22B.

In the fourth embodiment, first electrode layers 11Ag, second electrode layers 11Bg and intermediate insulating layers 10g are laminated alternately without forming the first and second end-portion insulating layers 12A and 12B, and an insulative protection layer (solder resist, for example) 5g for covering the first and second land portions 22A and 22B is formed so that only the portions in which the first land portion 22A and the first electrode layers 11Ag are connected to each other and the portions in which the second land portion 22B and the second electrode layers 11B are connected to each other are exposed from first openings 51A and second openings 51B of the protection layer 5g, respectively, to prevent a short-circuit between the first and second electrode layers 11A and 11B. In this fourth embodiment, the first electrode layers 11Ag and the second electrode layers 11Bg are not only connected respectively to the first land portion 22A and the second land portion 22B through the first junction means 23A and the second junction means 23B, respectively, but also serve to fix the laminated body 1g to the surface of the insulating substrate 3. The first and second junction means 23A and 23B may be soldering or brazing.

Figure 18A:
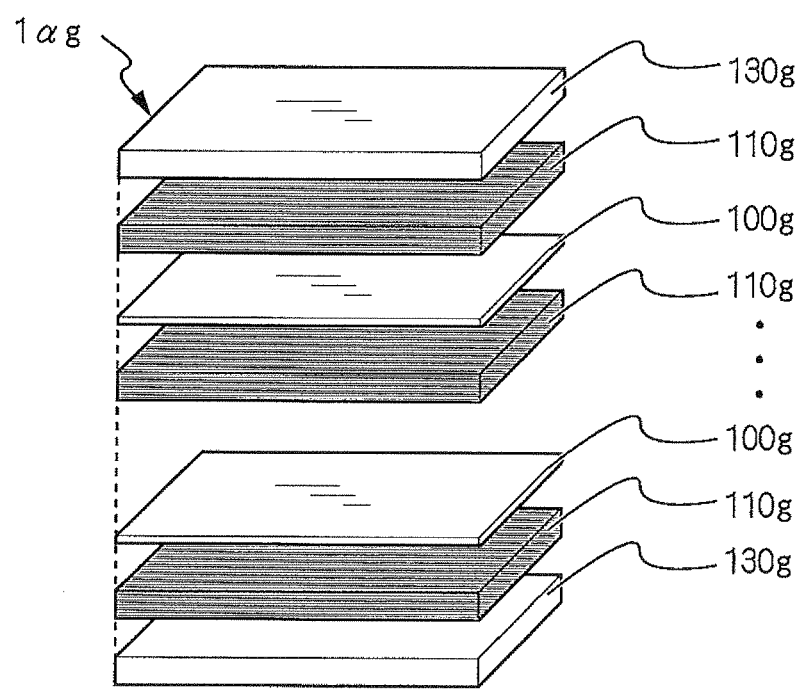
FIG. 18A is a diagram showing a laminating step included in a method of manufacturing the PM detection element according to the fourth embodiment of the invention.
Figure 18B:
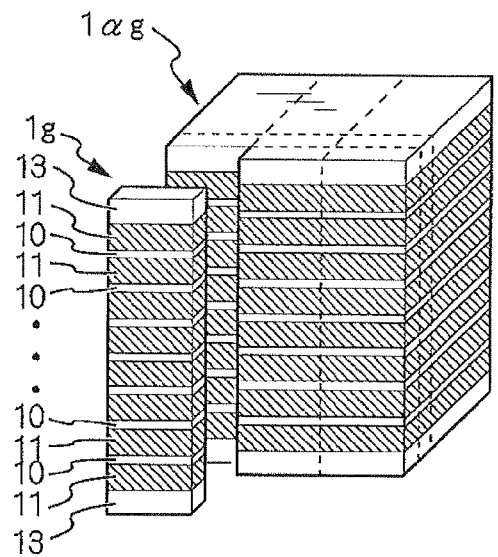
FIG. 18B is a perspective view for explaining a step of cutting out a laminated body performed after step shown in FIG. 18A.
Figure 18C:
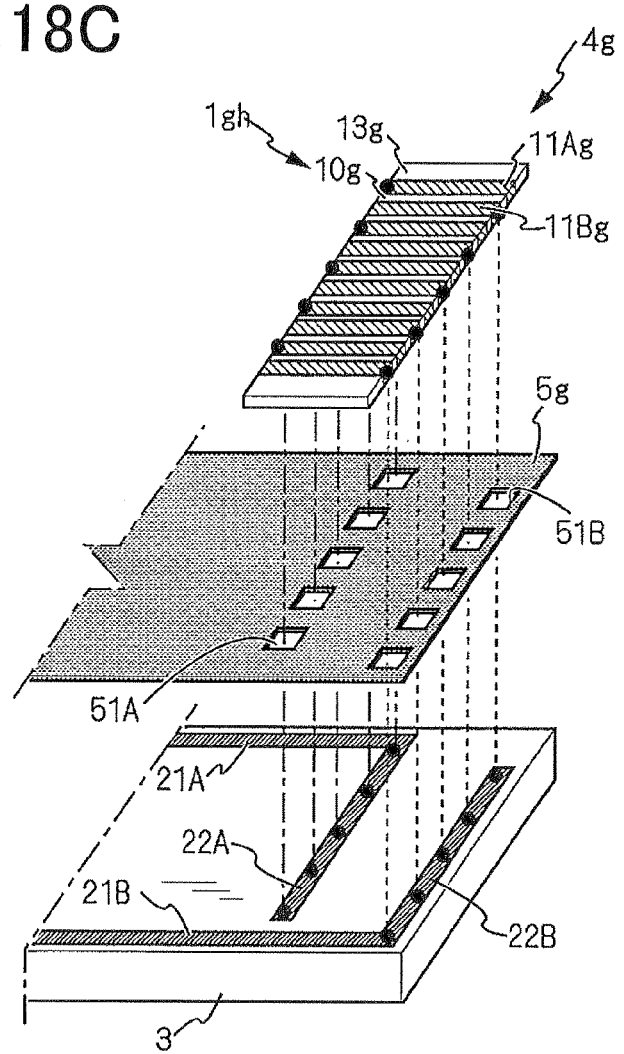
FIG. 18C is a perspective view for explaining a mounting step performed after the step shown in FIG. 18B.

In this embodiment, as shown in FIG. 18A, electrode layer green sheets 110g constituting the first and second electrode layers 11Ag and 11Bg and insulating layer green sheets 100g constituting the intermediate insulating layers 10 are laminated alternately. Thereafter, an insulating layer green sheet 130g is laminated on each of the end surfaces of this lamination to obtain a laminated body set 1αg. By cutting the obtained laminated body set 1αg into even pieces, the laminated body 1g as shown in FIG. 18B is obtained. In the foregoing embodiments, the first electrode layers 11A and the second electrode layers 11B are drawn alternately to the opposite lateral sides of the laminated body, and the first and second end-portion insulating layers 12A and 12B are formed in order to prevent the first land portion 22A from being erroneously connected to the second electrode layers 11B, or prevent the second land portion 22B from being erroneously connected to the first electrode layers 11A. In this embodiment, as shown in FIG. 18C, the first electrode layers 11Ag and the second electrode layers 11Bg are exposed respectively to the opposite lateral sides of the laminated body 1g while being separated from each other by the very thin intermediate insulating layers 10g, and they are covered entirely by the protection layer 5g except the portions in which they are connected to the land portions. Accordingly, only the first land portion 22A exposed from the first openings 51A of the protection layer 5g can be connected to the first electrode layers 11Ag, and only the second land portion 22B exposed from the second openings 513 of the protection layer 5g can be connected to the second electrode layers 11Bg. Incidentally, since the thickness $t_{EL}$ of the first and second electrode layers 11Ag and 11Bg is greater than 100 μm, the first and second openings 51A and 51B may be formed at intervals of about 100 μm in a shape of a rectangle whose sides are 50 to 100 μm long. Accordingly, the protection layer 5g can be formed with a high degree of accuracy by a common thick film printing method. According to this embodiment, since it is not necessary to provide the insulating layers 12A and 12B for the electrode layers 11A and 11B unlike the foregoing embodiments, although the laminated body 1g can be formed in the very simple way, the obtained PM detection element 4g has a very small dead mass enabling to detect trace amount of PM with a high degree of accuracy.

Figure 19:
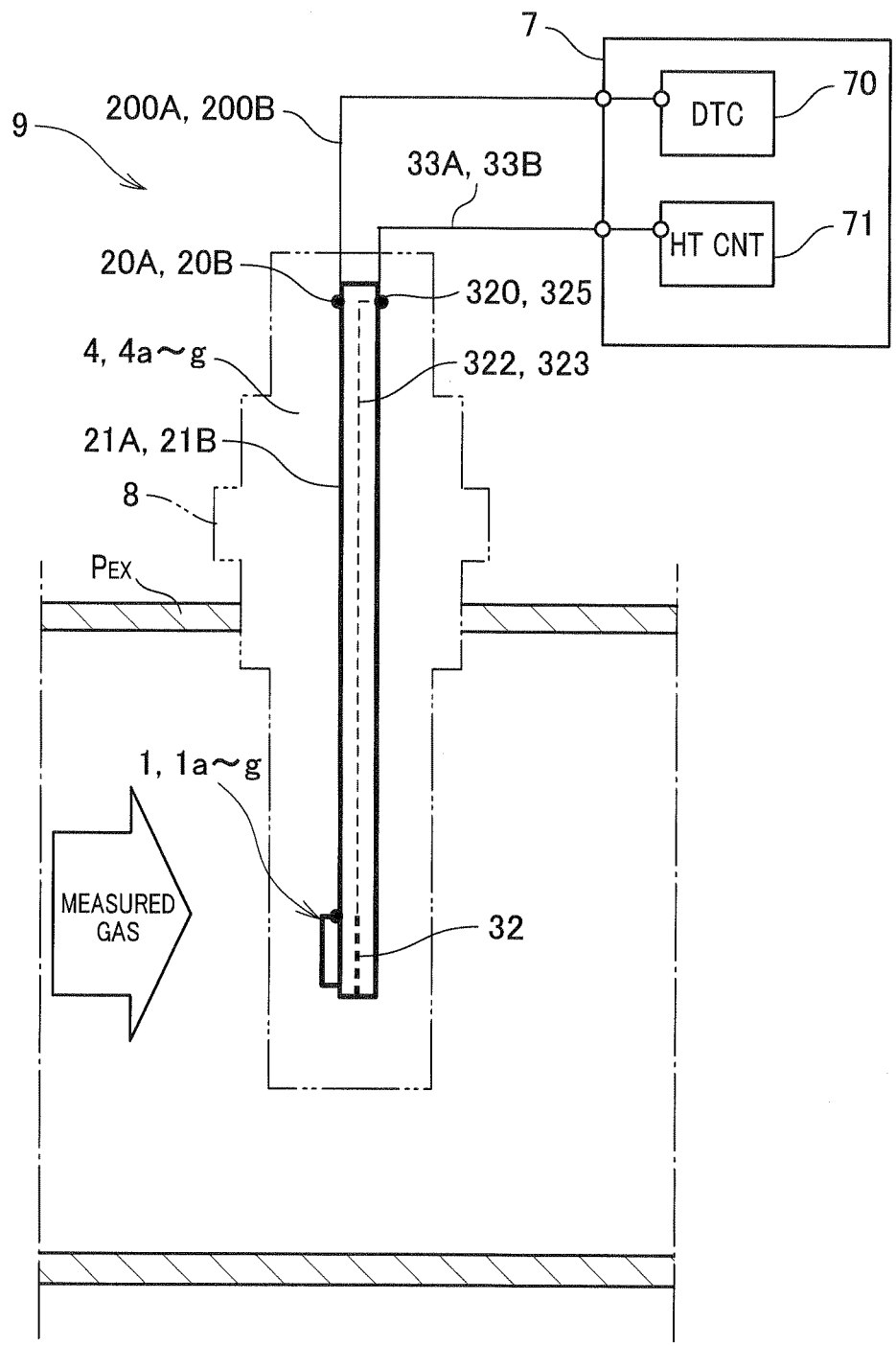
FIG. 19 is a diagram schematically showing a PM detection sensor including the PM detection element of the invention.

Next, a PM detection sensor 9 having one of the PM detection elements 4 and 4a to 4g is described with reference to FIG. 19. The PM detection sensor 9 includes one of the PM detection elements 4 and 4a to 4g, a housing 8 and a control section 7. The housing 8 is for holding one of the laminated body 1 and 1a to 1g serving as a detecting section of the PM detection element in a measurement gas passage $P_{EX}$, for example, an exhaust gas passage of an internal combustion engine (not shown). The structure of the housing 8 is not limited to any specific structure. The front end of the PM detection element of the PM detection sensor 9 may be covered by a protection cover (not shown). The control section 7 includes an electrical characteristic measuring means (DTC) 70 for measuring one of the resistance, capacitance or impedance which vary depending on the amount of PM collected between the pair of the detection electrodes, a heat generating-body 32 and a heat-generating body control means (HT CNT) 71 for controlling current supply to the heat-generating body 32 to heat the PM detection element to a desired temperature. The terminal portions 20A and 20B of the PM detection element are connected to the electrical characteristic measuring means 70 through a pair of signal wires 200A and 200B. Heater terminal portions 320 and 325 of the PM detection element are connected to the heat-generating body control means 71 through a pair of current supply wires 33A and 33B. The PM detection sensor 9 of the present invention has a very small dead mass, and therefore can detect emission of PM from immediately after start of the internal combustion engine. Further, not only the PM detection sensor 9 of the present invention can quantitatively detect PM with a very high degree of accuracy, but also has a high durability because it has the structure in which the cross-sectional surface of the laminated body (1, 1a to 1g) constituted of the electrode layers 11A and 11B laminated alternately is used as the detection surface, unlike the conventional structure in which the detection electrodes are film-formed on the substrate surface in a comb-like shape.

The above explained preferred embodiments are exemplary of the invention of the present application which is described solely by the claims appended below. It should be understood that modifications of the preferred embodiments may be made as would occur to one of skill in the art.

What is claimed is:

1. A particulate matter detection element for detecting particulate matter contained in a measured gas comprising:
an electrode layer laminated body which is made up of a plurality of first electrode layers, a plurality of second electrode layers, and a plurality of intermediate insulating layers, the first electrode layers and the second electrode layers being stacked to overlap each other in a lamination direction with each of the intermediate insulating layers being disposed between one of the first electrode layers and an adjacent one of the second electrode layers, thereby forming a detection surface and a mounting surface of the electrode layer laminated body, the detection surface and the mounting surface being opposed to each other through a thickness of the electrode layer laminated body in a direction perpendicular to the lamination direction and towards an electrode drawing layer,
the electrode drawing layer including a first electrical conductor and a second electrical conductor configured to transmit a signal via an electrical connection, the signal representing one of a resistance, a capacitance and a impedance between each of the first electrode layers and an adjacent one of the second electrode layers as an electrical characteristic varying depending on an amount of particulate matter present between the pair of the detection electrodes;

wherein the first and second electrode layers and the intermediate insulating layers each have a plate-like shape and a thickness in a range between 3 μm and 20 μm, the detection surface of the electrode layer laminated body is exposed to outside, the mounting surface is in physical contact with an insulating substrate, and the first electrode layers are electrically connected to the first electrical conductors through respective electrical joints, and the second electrode layers are electrically connected to the second electrical conductor through respective electrical joints.

2. The particulate matter detection element according to claim 1, further comprising a first end-portion insulating layer covering one end of the first electrode layer on a first side of the electrode laminated body, and a second end-portion insulating layer covering one end of the second electrode layer on a second side opposite to the first side of the electrode laminated body, so that the first electrode layer is electrically connected externally and the second electrode layer is insulated from outside on the second side, and the second electrode layer is electrically connected to outside and the first electrode layer is insulated from outside on the first side.

3. The particulate matter detection element according to claim 2, further comprising a first electrode connected with the first electrode layer on the second side of the electrode laminated body and a second electrode connected with the second electrode layer on the first side of the electrode laminated body.

4. The particulate matter detection element according to claim 3, wherein the insulating substrate has a plate-like shape, the electrode drawing layer including:

first and second land portions formed on the insulating substrate and holding the electrode laminated body, the first land portion being connected to the first electrode layer, the second land portion being connected to the second electrode layer;

first and second lead portions connected to the first land portion and the second land portion, respectively; and first and second terminal portions connected to the first lead portion and the second lead portion, respectively.

5. The particulate matter detection element according to claim 4, wherein a protection layer having an opening and made of an insulating material is formed on a surface of the insulating substrate so as to cover the detection surface such that only a portion of the detection surface in which the first and second electrode layers and the intermediate insulating layer extend in parallel to one another is exposed from the opening of the protection layer.

6. The particulate matter detection element according to claim 4, wherein an insulative protection layer having first and second openings is formed on a surface of the insulating substrate such that only a portion in which the first electrode layer and the first land portion are connected to each other is exposed from the first opening, and only a portion in which the second electrode layer and the second land portion are connected to each other is exposed from the second opening.

7. The particulate matter detection element according to claim 1, wherein the first and second electrode layers are made of a perovskite-type conductive oxide material having an electrical conductivity of higher than $10^{-2}$ S/cm selected from LNF (LaNi$_{0.6}$Fe$_{0.4}$O$_3$), LSN (La$_{1.2}$Sr$_{0.8}$NiO$_4$), LSM (La$_{1-x}$Sr$_x$MnO$_{3-\delta}$), LSC (La$_{1-x}$Sr$_x$CoO$_{3-\delta}$), LCC (La$_{1-x}$Ca$_x$CrO$_{3-\delta}$), and LSCN (La$_{0.85}$Sr$_{0.15}$Cr$_{1-x}$Ni$_x$O$_{3-\delta}$) ($0.1 \leq X \leq 0.7$).

8. The particulate matter detection element according to claim 1, wherein the intermediate insulating layer is made of an insulating oxide material having an electrical conductivity of lower than $10^{-5}$ S/cm selected from a partially stabilized zirconia typified by 8YSZ((ZrO$_2$2)$_{0.82}$(Y$_2$O$_3$3)$_{0.08}$), MgO and Al$_2$O$_3$.

9. A particulate matter detection sensor comprising:

the particulate material detection element as recited in claim 1; and a processor configured to determine an amount of particulate matter collected between the pair of the detection electrodes based on the signal transmitted through the electrode drawing layer.

10. The particulate matter detection element according to claim 1, wherein the first and second electrode layers each have a thickness in a range between 50 μm and 500 μm.

* * * * *